US006107063A

United States Patent [19]

Moeckel et al.

[11] Patent Number: 6,107,063

[45] Date of Patent: Aug. 22, 2000

[54] PRODUCTION OF L-ISOLEUCINE BY MEANS OF RECOMBINANT MICROORGANISMS WITH DEREGULATED THREONINE DEHYDRATASE

[75] Inventors: Bettina Moeckel, Duesseldorf; Lothar Eggeling; Hermann Sahm, both of Juelich, all of Germany

[73] Assignee: Forschungszentrum Juelich GmbH, Juelich, Germany

[21] Appl. No.: 08/669,378

[22] PCT Filed: Jan. 9, 1995

[86] PCT No.: PCT/DE95/00017

§ 371 Date: Mar. 20, 1997

§ 102(e) Date: Mar. 20, 1997

[87] PCT Pub. No.: WO95/19442

PCT Pub. Date: Jul. 20, 1995

[30] Foreign Application Priority Data

Jan. 14, 1994 [DE] Germany ............................ 44 00 926

[51] Int. Cl.[7] ............................ C12P 13/06; C12N 1/21; C12N 15/31; C12N 15/63

[52] U.S. Cl. ............... 435/116; 435/252.32; 435/252.33; 435/320.1; 536/23.2; 536/23.7

[58] Field of Search ................................ 435/116, 252.3, 435/252.32, 252.33, 320.1; 536/23.1, 23.2, 23.7

[56] References Cited

FOREIGN PATENT DOCUMENTS

0436886A1 7/1991 European Pat. Off. .
WO 87/02984 5/1987 WIPO .
WO87/02984 5/1987 WIPO .

OTHER PUBLICATIONS

Gavrilova et al., Chemical Abstracts 108(144395d): 176 (1988).

Moeckel et al., Chemical Abstracts 121(199457z): 554(1994).

Cordes et al. (1992) Cloning, organization and functional analysis of ilvA, ilvB and ilvC genes from *Corynebacterium glutamicum*. Gene 112:113–116, 1992.

Komatsubara et al. (1980) Transductional construction of an isoleucine–producing strain of *Serratia marcescens*. J. Gen. Microbiol. 119:51–61, Jul. 1980.

*Primary Examiner*—George C. Elliott
*Assistant Examiner*—Robert Schwartzman
*Attorney, Agent, or Firm*—Foley & Lardner

[57] ABSTRACT

The invention relates to processes for the microbial production of L-isoleucine. To this end, in a gene in vitro of a threonine dehydratse, one or more bases in the gene region coding the enzyme's allosteric domains are exchanged in such a way that at least one amino acid in the amino acid sequence of the allosteric domains of the enzyme is replaced by another so that the enzyme is no longer inhibited by L-isoleucine feedback. Furthermore, concrete amino acid exchanges in the amino acid sequence of the enzyme are effected in a gene in vitro of a threonin dehydratase of *Corynebacterium glutamicum* by base exchange both outside and inside and outside the gene region coding the allosteric domains of the enzyme si that, after the transformation of such mutated threonine dehydratase genes into a threonine or L-isoleucine-producing host cell, the latter repeatedly forms L-isoleucine.

22 Claims, 3 Drawing Sheets

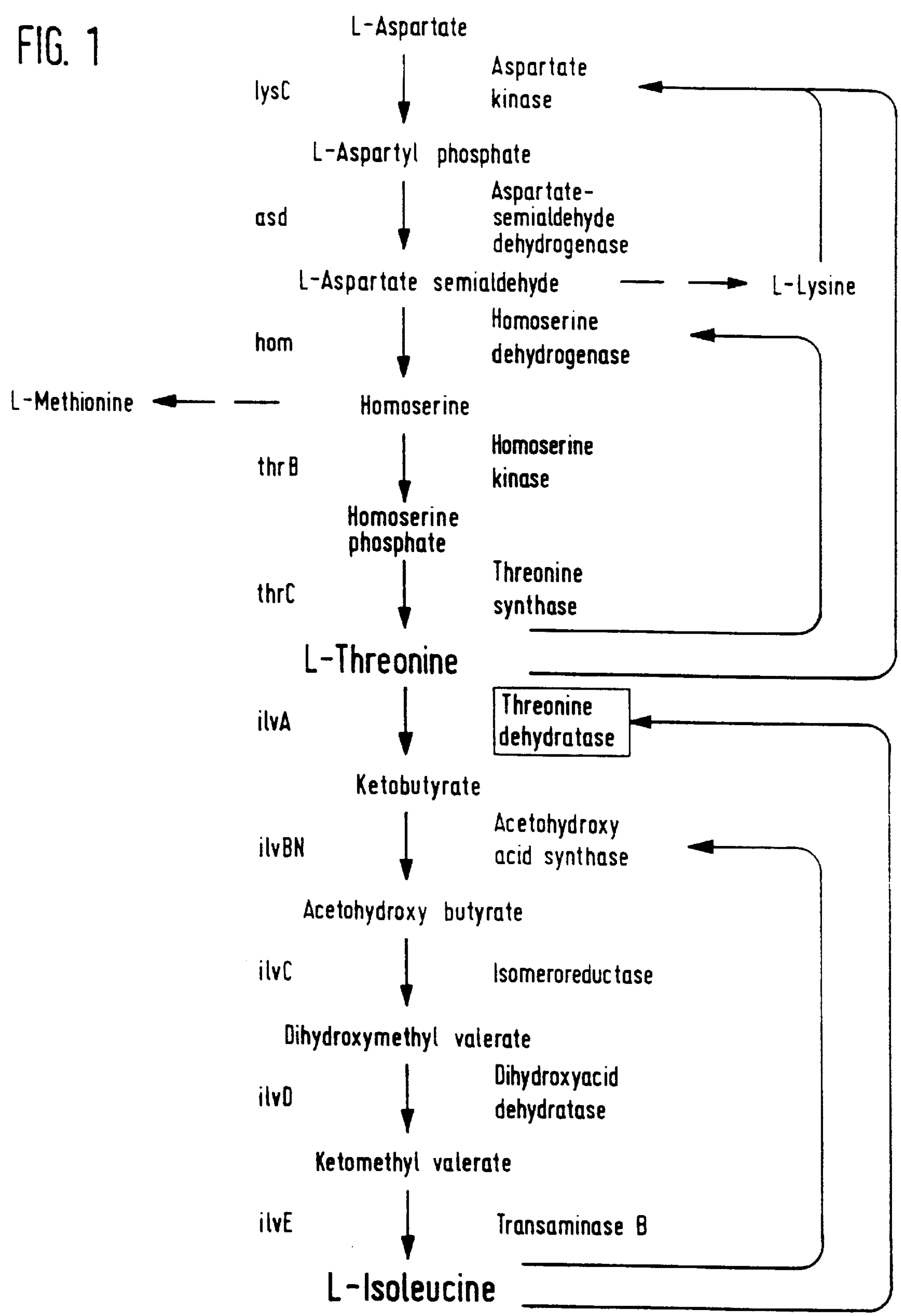
FIG. 1
L-Aspartate
lysC
Aspartate kinase
L-Aspartyl phosphate
asd
Aspartate-semialdehyde dehydrogenase
L-Aspartate semialdehyde
L-Lysine
hom
Homoserine dehydrogenase
L-Methionine
Homoserine
thrB
Homoserine kinase
Homoserine phosphate
thrC
Threonine synthase
L-Threonine
ilvA
Threonine dehydratase
Ketobutyrate
ilvBN
Acetohydroxy acid synthase
Acetohydroxy butyrate
ilvC
Isomeroreductase
Dihydroxymethyl valerate
ilvD
Dihydroxyacid dehydratase
Ketomethyl valerate
ilvE
Transaminase B
L-Isoleucine

SEQUENCE LISTING

```
(1) GENERAL INFORMATION:

   (iii) NUMBER OF SEQUENCES: 18


(2) INFORMATION FOR SEQ ID NO:1:

     (i) SEQUENCE CHARACTERISTICS:
          (A) LENGTH: 1925 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 432..1739

        (xi) SEQUENCE DESCRIPTION: SEQ ID NO:1:

CGCCATTGCT GAGCATTGAG CTGCCTTCAG AGCTGCCTGG CCAGGTTTCG TTTCCATCGA     60

CTGGATTTCC ATCATCATCA AGGATCTGTG ATGAGGTGAT GTTGTCTGAG AGCTGTGTCA    120

GTGCGTCAGA GGACTGAGCC TGGGCAACTG GAGTGAACAC GGACAATGCC ACAGCGCTTG    180

CTGTAACAAG GGTCAAAGTA CTTCGACGCA AAGACAAAAC TTTTCTCCTG GCAATAAATA    240

TGCGGATTTA CTATGGAAAC AAGATAGAAG ATTGGATAGC GAAAGCTATC CTCAACTCGT    300

GGAAAGTGTA GTGCCACAAC CACAGTATTG GCTAGAAAAC AATCTATAGC ATTGTTCTAC    360

AAAGAGCTTG TTGGAAATAA AACCTATGCC AAAGTAGGTG CAATTCTAGG AGAAGATTAC    420

ACTAGTCAAC C ATG AGT GAA ACA TAC GTG TCT GAG AAA AGT CCA GGA GTG     470
             Met Ser Glu Thr Tyr Val Ser Glu Lys Ser Pro Gly Val
               1               5                  10

ATG GCT AGC GGA GCG GAG CTG ATT CGT GCC GCC GAC ATT CAA ACG GCG      518
Met Ala Ser Gly Ala Glu Leu Ile Arg Ala Ala Asp Ile Gln Thr Ala
     15                  20                  25

CAG GCA CGA ATT TCC TCC GTC ATT GCA CCA ACT CCA TTG CAG TAT TGC      566
Gln Ala Arg Ile Ser Ser Val Ile Ala Pro Thr Pro Leu Gln Tyr Cys
 30                  35                  40                  45

CCT CGT CTT TCT GAG GAA ACC GGA GCG GAA ATC TAC CTT AAG CGT GAG      614
Pro Arg Leu Ser Glu Glu Thr Gly Ala Glu Ile Tyr Leu Lys Arg Glu
                 50                  55                  60

GAT CTG CAG GAT GTT CGT TCC TAC AAG ATC CGC GGT GCG CTG AAC TCT      662
Asp Leu Gln Asp Val Arg Ser Tyr Lys Ile Arg Gly Ala Leu Asn Ser
             65                  70                  75

GGA GCG CAG TCA CCC CAA GAG CAG CGC GAT GCA GGT ATC GTT GCC GCA      710
Gly Ala Gln Ser Pro Gln Glu Gln Arg Asp Ala Gly Ile Val Ala Ala
         80                  85                  90

TCT GCA GGT AAC CAT GCC CAG GGC GTG GCC TAT GTG TGC AAG TCC TTG      758
Ser Ala Gly Asn His Ala Gln Gly Val Ala Tyr Val Cys Lys Ser Leu
     95                 100                 105

GGC GTT CAG GGA CGC ATC TAT GTT CCT GTG CAG ACT CCA AAG CAA AAG      806
Gly Val Gln Gly Arg Ile Tyr Val Pro Val Gln Thr Pro Lys Gln Lys
110                 115                 120                 125

CGT GAC CGC ATC ATG GTT CAC GGC GGA GAG TTT GTC TCC TTG GTG GTC      854
Arg Asp Arg Ile Met Val His Gly Gly Glu Phe Val Ser Leu Val Val
                130                 135                 140

ACT GGC AAT AAC TTC GAC GAA GCA TCG GCT GCA GCG CAT GAA GAT GCA      902
Thr Gly Asn Asn Phe Asp Glu Ala Ser Ala Ala Ala His Glu Asp Ala
            145                 150                 155

GAG CGC ACC GGC GCA ACG CTG ATC GAG CCT TTC GAT GCT CGC AAC ACC      950
```

-continued

```
Glu Arg Thr Gly Ala Thr Leu Ile Glu Pro Phe Asp Ala Arg Asn Thr
        160                 165                 170

GTC ATC GGT CAG GGC ACC GTG GCT GCT GAG ATC TTG TCG CAG CTG ACT      998
Val Ile Gly Gln Gly Thr Val Ala Ala Glu Ile Leu Ser Gln Leu Thr
    175                 180                 185

TCC ATG GGC AAG AGT GCA GAT CAC GTG ATG GTT CCA GTC GGC GGT GGC     1046
Ser Met Gly Lys Ser Ala Asp His Val Met Val Pro Val Gly Gly Gly
190                 195                 200                 205

GGA CTT CTT GCA GGT GTG GTC AGC TAC ATG GCT GAT ATG GCA CCT CGC     1094
Gly Leu Leu Ala Gly Val Val Ser Tyr Met Ala Asp Met Ala Pro Arg
                210                 215                 220

ACT GCG ATC GTT GGT ATC GAA CCA GCG GGA GCA GCA TCC ATG CAG GCT     1142
Thr Ala Ile Val Gly Ile Glu Pro Ala Gly Ala Ala Ser Met Gln Ala
            225                 230                 235

GCA TTG CAC AAT GGT GGA CCA ATC ACT TTG GAG ACT GTT GAT CCC TTT     1190
Ala Leu His Asn Gly Gly Pro Ile Thr Leu Glu Thr Val Asp Pro Phe
        240                 245                 250

GTG GAC GGC GCA GAG GTC AAA CGT GTC GGA GAT CTC AAC TAC ACC ATC     1238
Val Asp Gly Ala Glu Val Lys Arg Val Gly Asp Leu Asn Tyr Thr Ile
    255                 260                 265

GTG GAG AAG AAC CAG GGT CGC GTG CAC ATG ATG AGC GCG ACC GAG GGC     1286
Val Glu Lys Asn Gln Gly Arg Val His Met Met Ser Ala Thr Glu Gly
270                 275                 280                 285

GCT GTG TGT ACT GAG ATG CTC GAT CTT TAC CAA AAC GAA GGC ATC ATC     1334
Ala Val Cys Thr Glu Met Leu Asp Leu Tyr Gln Asn Glu Gly Ile Ile
                290                 295                 300

GCG GAG CCT GCT GGC GCG CTG TCT ATC GCT GGG TTG AAG GAA ATG TCC     1382
Ala Glu Pro Ala Gly Ala Leu Ser Ile Ala Gly Leu Lys Glu Met Ser
            305                 310                 315

TTT GCA CCT GGT TCT GCC GTG GTG TGC ATC ATC TCT GGT GGC AAC AAC     1430
Phe Ala Pro Gly Ser Ala Val Val Cys Ile Ile Ser Gly Gly Asn Asn
        320                 325                 330

GAT GTG CTG CGT TAT GCG GAA ATC GCT GAG CGC TCC TTG GTG CAC CGC     1478
Asp Val Leu Arg Tyr Ala Glu Ile Ala Glu Arg Ser Leu Val His Arg
    335                 340                 345

GGT TTG AAG CAC TAC TTC TTG GTG AAC TTC CCG CAA AAG CCT GGT CAG     1526
Gly Leu Lys His Tyr Phe Leu Val Asn Phe Pro Gln Lys Pro Gly Gln
350                 355                 360                 365

TTG CGT CAC TTC CTG GAA GAT ATC CTG GGA CCG GAT GAT GAC ATC ACG     1574
Leu Arg His Phe Leu Glu Asp Ile Leu Gly Pro Asp Asp Asp Ile Thr
                370                 375                 380

CTG TTT GAG TAC CTC AAG CGC AAC AAC CGT GAG ACC GGT ACT GCG TTG     1622
Leu Phe Glu Tyr Leu Lys Arg Asn Asn Arg Glu Thr Gly Thr Ala Leu
            385                 390                 395

GTG GGT ATT CAC TTG AGT GAA GCA TCA GGA TTG GAT TCT TTG CTG GAA     1670
Val Gly Ile His Leu Ser Glu Ala Ser Gly Leu Asp Ser Leu Leu Glu
        400                 405                 410

CGT ATG GAG GAA TCG GCA ATT GAT TCC CGT CGC CTC GAG CCG GGC ACT     1718
Arg Met Glu Glu Ser Ala Ile Asp Ser Arg Arg Leu Glu Pro Gly Thr
    415                 420                 425

CCT GAG TAC GAA TAC TTG ACC TAAACATAGC TGAAGGCCAC CTCAATCGAG        1769
Pro Glu Tyr Glu Tyr Leu Thr
430                 435

GTGGCCTTTT TCTAGTTTCG GGTCAGGATC GCAAAGCCCC ACGGCTGAAG GGTTGTGGAG   1829

GTGTCGGTGA CGGTGGGGGA AGTGAAGCTG TAAATCAGCT CGCCGCCAAG CGGGACGGTG   1889

ATGGTGTCGT CGGAGAAATT CGCCAGAATT CGGCCG                             1925
```

(2) INFORMATION FOR SEQ ID NO:2:

-continued

```
    (i) SEQUENCE CHARACTERISTICS:
         (A) LENGTH: 436 amino acids
         (B) TYPE: amino acid
         (D) TOPOLOGY: linear

   (ii) MOLECULE TYPE: protein

   (xi) SEQUENCE DESCRIPTION: SEQ ID NO:2:

Met Ser Glu Thr Tyr Val Ser Glu Lys Ser Pro Gly Val Met Ala Ser
  1               5                  10                  15

Gly Ala Glu Leu Ile Arg Ala Ala Asp Ile Gln Thr Ala Gln Ala Arg
             20                  25                  30

Ile Ser Ser Val Ile Ala Pro Thr Pro Leu Gln Tyr Cys Pro Arg Leu
         35                  40                  45

Ser Glu Glu Thr Gly Ala Glu Ile Tyr Leu Lys Arg Glu Asp Leu Gln
     50                  55                  60

Asp Val Arg Ser Tyr Lys Ile Arg Gly Ala Leu Asn Ser Gly Ala Gln
 65                  70                  75                  80

Ser Pro Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Glu Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Ala Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365
```

-continued

```
Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

(2) INFORMATION FOR SEQ ID NO:3:

(i) SEQUENCE CHARACTERISTICS:
(A) LENGTH: 1925 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 432..1739

(xi) SEQUENCE DESCRIPTION: SEQ ID NO:3:

```
CGCCATTGCT GAGCATTGAG CTGCCTTCAG AGCTGCCTGG CCAGGTTTCG TTTCCATCGA      60

CTGGATTTCC ATCATCATCA AGGATCTGTG ATGAGGTGAT GTTGTCTGAG AGCTGTGTCA     120

GTGCGTCAGA GGACTGAGCC TGGGCAACTG GAGTGAACAC GGACAATGCC ACAGCGCTTG     180

CTGTAACAAG GGTCAAAGTA CTTCGACGCA AAGACAAAAC TTTTCTCCTG GCAATAAATA     240

TGCGGATTTA CTATGGAAAC AAGATAGAAG ATTGGATAGC GAAAGCTATC CTCAACTCGT     300

GGAAAGTGTA GTGCCACAAC CACAGTATTG GCTAGAAAAC AATCTATAGC ATTGTTCTAC     360

AAAGAGCTTG TTGGAAATAA AACCTATGCC AAAGTAGGTG CAATTCTAGG AGAAGATTAC     420

ACTAGTCAAC C ATG AGT GAA ACA TAC GTG TCT GAG AAA AGT CCA GGA GTG      470
             Met Ser Glu Thr Tyr Val Ser Glu Lys Ser Pro Gly Val
               1               5                  10

ATG GCT AGC GGA GCG GAG CTG ATT CGT GCC GCC GAC ATT CAA ACG GCG      518
Met Ala Ser Gly Ala Glu Leu Ile Arg Ala Ala Asp Ile Gln Thr Ala
     15                  20                  25

CAG GCA CGA ATT TCC TCC GTC ATT GCA CCA ACT CCA TTG CAG TAT TGC      566
Gln Ala Arg Ile Ser Ser Val Ile Ala Pro Thr Pro Leu Gln Tyr Cys
 30                  35                  40                  45

CCT CGT CTT TCT GAG GAA ACC GGA GCG GAA ATC TAC CTT AAG CGT GAG      614
Pro Arg Leu Ser Glu Glu Thr Gly Ala Glu Ile Tyr Leu Lys Arg Glu
                 50                  55                  60

GAT CTG CAG GAT GTT CGT TCC TAC AAG ATC CGC GGT GCG CTG AAC TCT      662
Asp Leu Gln Asp Val Arg Ser Tyr Lys Ile Arg Gly Ala Leu Asn Ser
             65                  70                  75

GGA GCG CAG TCA CCC CAA GAG CAG CGC GAT GCA GGT ATC GTT GCC GCA      710
Gly Ala Gln Ser Pro Gln Glu Gln Arg Asp Ala Gly Ile Val Ala Ala
         80                  85                  90

TCT GCA GGT AAC CAT GCC CAG GGC GTG GCC TAT GTG TGC AAG TCC TTG      758
Ser Ala Gly Asn His Ala Gln Gly Val Ala Tyr Val Cys Lys Ser Leu
     95                 100                 105

GGC GTT CAG GGA CGC ATC TAT GTT CCT GTG CAG ACT CCA AAG CAA AAG      806
Gly Val Gln Gly Arg Ile Tyr Val Pro Val Gln Thr Pro Lys Gln Lys
110                 115                 120                 125

CGT GAC CGC ATC ATG GTT CAC GGC GGA GAG TTT GTC TCC TTG GTG GTC      854
```

-continued

```
Arg Asp Arg Ile Met Val His Gly Gly Glu Phe Val Ser Leu Val Val
                130                 135                 140

ACT GGC AAT AAC TTC GAC GAA GCA TCG GCT GCA GCG CAT GAA GAT GCA      902
Thr Gly Asn Asn Phe Asp Glu Ala Ser Ala Ala Ala His Glu Asp Ala
            145                 150                 155

GAG CGC ACC GGC GCA ACG CTG ATC GAG CCT TTC GAT GCT CGC AAC ACC      950
Glu Arg Thr Gly Ala Thr Leu Ile Glu Pro Phe Asp Ala Arg Asn Thr
        160                 165                 170

GTC ATC GGT CAG GGC ACC GTG GCT GCT GAG ATC TTG TCG CAG CTG ACT      998
Val Ile Gly Gln Gly Thr Val Ala Ala Glu Ile Leu Ser Gln Leu Thr
    175                 180                 185

TCC ATG GGC AAG AGT GCA GAT CAC GTG ATG GTT CCA GTC GGC GGT GGC     1046
Ser Met Gly Lys Ser Ala Asp His Val Met Val Pro Val Gly Gly Gly
190                 195                 200                 205

GGA CTT CTT GCA GGT GTG GTC AGC TAC ATG GCT GAT ATG GCA CCT CGC     1094
Gly Leu Leu Ala Gly Val Val Ser Tyr Met Ala Asp Met Ala Pro Arg
                210                 215                 220

ACT GCG ATC GTT GGT ATC GAA CCA GCG GGA GCA GCA TCC ATG CAG GCT     1142
Thr Ala Ile Val Gly Ile Glu Pro Ala Gly Ala Ala Ser Met Gln Ala
            225                 230                 235

GCA TTG CAC AAT GGT GGA CCA ATC ACT TTG GAG ACT GTT GAT CCC TTT     1190
Ala Leu His Asn Gly Gly Pro Ile Thr Leu Glu Thr Val Asp Pro Phe
        240                 245                 250

GTG GAC GGC GCA GAG GTC AAA CGT GTC GGA GAT CTC AAC TAC ACC ATC     1238
Val Asp Gly Ala Glu Val Lys Arg Val Gly Asp Leu Asn Tyr Thr Ile
    255                 260                 265

GTG GAG AAG AAC CAG GGT CGC GTG CAC ATG ATG AGC GCG ACC GAG GGC     1286
Val Glu Lys Asn Gln Gly Arg Val His Met Met Ser Ala Thr Glu Gly
270                 275                 280                 285

GCT GTG TGT ACT GAG ATG CTC GAT CTT TAC CAA AAC GAA GGC ATC ATC     1334
Ala Val Cys Thr Glu Met Leu Asp Leu Tyr Gln Asn Glu Gly Ile Ile
                290                 295                 300

GCG GAG CCT GCT GGC GCG CTG TCT ATC GCT GGG TTG AAG GAA ATG TCC     1382
Ala Glu Pro Ala Gly Ala Leu Ser Ile Ala Gly Leu Lys Glu Met Ser
            305                 310                 315

TTT GCA CCT GGT TCT GTC GTG GTG TGC ATC ATC TCT GGT GGC AAC AAC     1430
Phe Ala Pro Gly Ser Val Val Val Cys Ile Ile Ser Gly Gly Asn Asn
        320                 325                 330

GAT GTG CTG CGT TAT GCG GAA ATC GCT GAG CGC TCC TTG GTG CAC CGC     1478
Asp Val Leu Arg Tyr Ala Glu Ile Ala Glu Arg Ser Leu Val His Arg
    335                 340                 345

GGT TTG AAG CAC TAC TTC TTG GTG AAC TTC CCG CAA AAG CCT GGT CAG     1526
Gly Leu Lys His Tyr Phe Leu Val Asn Phe Pro Gln Lys Pro Gly Gln
350                 355                 360                 365

TTG CGT CAC TTC CTG GAA GAT ATC CTG GGA CCG GGT GAT GAC ATC ACG     1574
Leu Arg His Phe Leu Glu Asp Ile Leu Gly Pro Gly Asp Asp Ile Thr
                370                 375                 380

CTG TTT GAG TAC CTC AAG CGC AAC AAC CGT GAG ACC GGT ACT GCG TTG     1622
Leu Phe Glu Tyr Leu Lys Arg Asn Asn Arg Glu Thr Gly Thr Ala Leu
            385                 390                 395

GTG GGT ATT CAC TTG AGT GAA GCA TCA GGA TTG GAT TCT TTG CTG GAA     1670
Val Gly Ile His Leu Ser Glu Ala Ser Gly Leu Asp Ser Leu Leu Glu
        400                 405                 410

CGT ATG GAG GAA TCG GCA ATT GAT TCC CGT CGC CTC GAG CCG GGC ACT     1718
Arg Met Glu Glu Ser Ala Ile Asp Ser Arg Arg Leu Glu Pro Gly Thr
    415                 420                 425

CCT GAG TAC GAA TAC TTG ACC TAAACATAGC TGAAGGCCAC CTCAATCGAG        1769
Pro Glu Tyr Glu Tyr Leu Thr
430                 435
```

-continued

```
GTGGCCTTTT TCTAGTTTCG GGTCAGGATC GCAAAGCCCC ACGGCTGAAG GGTTGTGGAG   1829

GTGTCGGTGA CGGTGGGGGA AGTGAAGCTG TAAATCAGCT CGCCGCCAAG CGGGACGGTG   1889

ATGGTGTCGT CGGAGAAATT CGCCAGAATT CGGCCG                             1925
```

(2) INFORMATION FOR SEQ ID NO:4:

(i) SEQUENCE CHARACTERISTICS:
(A) LENGTH: 436 amino acids
(B) TYPE: amino acid
(D) TOPOLOGY: linear (ii) MOLECULE TYPE: protein (xi) SEQUENCE DESCRIPTION: SEQ ID NO:4:

```
Met Ser Glu Thr Tyr Val Ser Glu Lys Ser Pro Gly Val Met Ala Ser
  1               5                  10                  15

Gly Ala Glu Leu Ile Arg Ala Ala Asp Ile Gln Thr Ala Gln Ala Arg
             20                  25                  30

Ile Ser Ser Val Ile Ala Pro Thr Pro Leu Gln Tyr Cys Pro Arg Leu
         35                  40                  45

Ser Glu Glu Thr Gly Ala Glu Ile Tyr Leu Lys Arg Glu Asp Leu Gln
     50                  55                  60

Asp Val Arg Ser Tyr Lys Ile Arg Gly Ala Leu Asn Ser Gly Ala Gln
 65                  70                  75                  80

Ser Pro Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Glu Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
```

-continued

```
            325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Gly Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

(2) INFORMATION FOR SEQ ID NO:5:

(i) SEQUENCE CHARACTERISTICS:
(A) LENGTH: 1925 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 432..1739

(xi) SEQUENCE DESCRIPTION: SEQ ID NO:5:

```
CGCCATTGCT GAGCATTGAG CTGCCTTCAG AGCTGCCTGG CCAGGTTTCG TTTCCATCGA     60

CTGGATTTCC ATCATCATCA AGGATCTGTG ATGAGGTGAT GTTGTCTGAG AGCTGTGTCA    120

GTGCGTCAGA GGACTGAGCC TGGGCAACTG GAGTGAACAC GGACAATGCC ACAGCGCTTG    180

CTGTAACAAG GGTCAAAGTA CTTCGACGCA AAGACAAAAC TTTTCTCCTG GCAATAAATA    240

TGCGGATTTA CTATGGAAAC AAGATAGAAG ATTGGATAGC GAAAGCTATC CTCAACTCGT    300

GGAAAGTGTA GTGCCACAAC CACAGTATTG GCTAGAAAAC AATCTATAGC ATTGTTCTAC    360

AAAGAGCTTG TTGGAAATAA AACCTATGCC AAAGTAGGTG CAATTCTAGG AGAAGATTAC    420

ACTAGTCAAC C ATG AGT GAA ACA TAC GTG TCT GAG AAA AGT CCA GGA GTG     470
             Met Ser Glu Thr Tyr Val Ser Glu Lys Ser Pro Gly Val
               1               5                  10

ATG GCT AGC GGA GCG GAG CTG ATT CGT GCC GCC GAC ATT CAA ACG GCG      518
Met Ala Ser Gly Ala Glu Leu Ile Arg Ala Ala Asp Ile Gln Thr Ala
     15                  20                  25

CAG GCA CGA ATT TCC TCC GTC ATT GCA CCA ACT CCA TTG CAG TAT TGC      566
Gln Ala Arg Ile Ser Ser Val Ile Ala Pro Thr Pro Leu Gln Tyr Cys
 30                  35                  40                  45

CCT CGT CTT TCT GAG GAA ACC GGA GCG GAA ATC TAC CTT AAG CGT GAG      614
Pro Arg Leu Ser Glu Glu Thr Gly Ala Glu Ile Tyr Leu Lys Arg Glu
                 50                  55                  60

GAT CTG CAG GAT GTT CGT TCC TAC AAG ATC CGC GGT GCG CTG AAC TCT      662
Asp Leu Gln Asp Val Arg Ser Tyr Lys Ile Arg Gly Ala Leu Asn Ser
             65                  70                  75

GGA GCG CAG TCA CCC CAA GAG CAG CGC GAT GCA GGT ATC GTT GCC GCA      710
Gly Ala Gln Ser Pro Gln Glu Gln Arg Asp Ala Gly Ile Val Ala Ala
         80                  85                  90

TCT GCA GGT AAC CAT GCC CAG GGC GTG GCC TAT GTG TGC AAG TCC TTG      758
```

-continued

```
Ser Ala Gly Asn His Ala Gln Gly Val Ala Tyr Val Cys Lys Ser Leu
     95                 100                 105

GGC GTT CAG GGA CGC ATC TAT GTT CCT GTG CAG ACT CCA AAG CAA AAG      806
Gly Val Gln Gly Arg Ile Tyr Val Pro Val Gln Thr Pro Lys Gln Lys
110                 115                 120                 125

CGT GAC CGC ATC ATG GTT CAC GGC GGA GAG TTT GTC TCC TTG GTG GTC      854
Arg Asp Arg Ile Met Val His Gly Gly Glu Phe Val Ser Leu Val Val
                130                 135                 140

ACT GGC AAT AAC TTC GAC GAA GCA TCG GCT GCA GCG CAT GAA GAT GCA      902
Thr Gly Asn Asn Phe Asp Glu Ala Ser Ala Ala Ala His Glu Asp Ala
            145                 150                 155

GAG CGC ACC GGC GCA ACG CTG ATC GAG CCT TTC GAT GCT CGC AAC ACC      950
Glu Arg Thr Gly Ala Thr Leu Ile Glu Pro Phe Asp Ala Arg Asn Thr
        160                 165                 170

GTC ATC GGT CAG GGC ACC GTG GCT GCT GAG ATC TTG TCG CAG CTG ACT      998
Val Ile Gly Gln Gly Thr Val Ala Ala Glu Ile Leu Ser Gln Leu Thr
    175                 180                 185

TCC ATG GGC AAG AGT GCA GAT CAC GTG ATG GTT CCA GTC GGC GGT GGC     1046
Ser Met Gly Lys Ser Ala Asp His Val Met Val Pro Val Gly Gly Gly
190                 195                 200                 205

GGA CTT CTT GCA GGT GTG GTC AGC TAC ATG GCT GAT ATG GCA CCT CGC     1094
Gly Leu Leu Ala Gly Val Val Ser Tyr Met Ala Asp Met Ala Pro Arg
                210                 215                 220

ACT GCG ATC GTT GGT ATC GAA CCA GCG GGA GCA GCA TCC ATG CAG GCT     1142
Thr Ala Ile Val Gly Ile Glu Pro Ala Gly Ala Ala Ser Met Gln Ala
            225                 230                 235

GCA TTG CAC AAT GGT GGA CCA ATC ACT TTG GAG ACT GTT GAT CCC TTT     1190
Ala Leu His Asn Gly Gly Pro Ile Thr Leu Glu Thr Val Asp Pro Phe
        240                 245                 250

GTG GAC GGC GCA GAG GTC AAA CGT GTC GGA GAT CTC AAC TAC ACC ATC     1238
Val Asp Gly Ala Glu Val Lys Arg Val Gly Asp Leu Asn Tyr Thr Ile
    255                 260                 265

GTG GAG AAG AAC CAG GGT CGC GTG CAC ATG ATG AGC GCG ACC GAG GGC     1286
Val Glu Lys Asn Gln Gly Arg Val His Met Met Ser Ala Thr Glu Gly
270                 275                 280                 285

GCT GTG TGT ACT GAG ATG CTC GAT CTT TAC CAA AAC GAA GGC ATC ATC     1334
Ala Val Cys Thr Glu Met Leu Asp Leu Tyr Gln Asn Glu Gly Ile Ile
                290                 295                 300

GCG GAG CCT GCT GGC GCG CTG TCT ATC GCT GGG TTG AAG GAA ATG TCC     1382
Ala Glu Pro Ala Gly Ala Leu Ser Ile Ala Gly Leu Lys Glu Met Ser
            305                 310                 315

TTT GCA CCT GGT TCT GTC GTG GTG TGC ATC ATC TCT GGT GGC AAC AAC     1430
Phe Ala Pro Gly Ser Val Val Val Cys Ile Ile Ser Gly Gly Asn Asn
        320                 325                 330

GAT GTG CTG CGT TAT GCG GAA ATC GCT GAG CGC TCC TTG GTG CAC CGC     1478
Asp Val Leu Arg Tyr Ala Glu Ile Ala Glu Arg Ser Leu Val His Arg
    335                 340                 345

GGT TTG AAG CAC TAC TTC TTG GTG AAC TTC CCG CAA AAG CCT GGT CAG     1526
Gly Leu Lys His Tyr Phe Leu Val Asn Phe Pro Gln Lys Pro Gly Gln
350                 355                 360                 365

TTG CGT CAC TTC CTG GAA GAT ATC CTG GGA CCG GAT GAT GAC ATC ACG     1574
Leu Arg His Phe Leu Glu Asp Ile Leu Gly Pro Asp Asp Asp Ile Thr
                370                 375                 380

CTG TGT GAG TAC CTC AAG CGC AAC AAC CGT GAG ACC GGT ACT GCG TTG     1622
Leu Cys Glu Tyr Leu Lys Arg Asn Asn Arg Glu Thr Gly Thr Ala Leu
            385                 390                 395

GTG GGT ATT CAC TTG AGT GAA GCA TCA GGA TTG GAT TCT TTG CTG GAA     1670
Val Gly Ile His Leu Ser Glu Ala Ser Gly Leu Asp Ser Leu Leu Glu
        400                 405                 410
```

-continued

```
CGT ATG GAG GAA TCG GCA ATT GAT TCC CGT CGC CTC GAG CCG GGC ACT      1718
Arg Met Glu Glu Ser Ala Ile Asp Ser Arg Arg Leu Glu Pro Gly Thr
    415                 420                 425

CCT GAG TAC GAA TAC TTG ACC TAAACATAGC TGAAGGCCAC CTCAATCGAG        1769
Pro Glu Tyr Glu Tyr Leu Thr
430                 435

GTGGCCTTTT TCTAGTTTCG GGTCAGGATC GCAAAGCCCC ACGGCTGAAG GGTTGTGGAG   1829

GTGTCGGTGA CGGTGGGGGA AGTGAAGCTG TAAATCAGCT CGCCGCCAAG CGGGACGGTG   1889

ATGGTGTCGT CGGAGAAATT CGCCAGAATT CGGCCG                             1925
```

(2) INFORMATION FOR SEQ ID NO:6:

(i) SEQUENCE CHARACTERISTICS:
(A) LENGTH: 436 amino acids
(B) TYPE: amino acid
(D) TOPOLOGY: linear (ii) MOLECULE TYPE: protein (xi) SEQUENCE DESCRIPTION: SEQ ID NO:6:

```
Met Ser Glu Thr Tyr Val Ser Glu Lys Ser Pro Gly Val Met Ala Ser
  1               5                  10                  15

Gly Ala Glu Leu Ile Arg Ala Ala Asp Ile Gln Thr Ala Gln Ala Arg
             20                  25                  30

Ile Ser Ser Val Ile Ala Pro Thr Pro Leu Gln Tyr Cys Pro Arg Leu
         35                  40                  45

Ser Glu Glu Thr Gly Ala Glu Ile Tyr Leu Lys Arg Glu Asp Leu Gln
     50                  55                  60

Asp Val Arg Ser Tyr Lys Ile Arg Gly Ala Leu Asn Ser Gly Ala Gln
 65                  70                  75                  80

Ser Pro Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Glu Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285
```

-continued

```
Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Cys Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

(2) INFORMATION FOR SEQ ID NO:7:

(i) SEQUENCE CHARACTERISTICS:
(A) LENGTH: 1925 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 432..1739

(xi) SEQUENCE DESCRIPTION: SEQ ID NO:7:

```
CGCCATTGCT GAGCATTGAG CTGCCTTCAG AGCTGCCTGG CCAGGTTTCG TTTCCATCGA      60

CTGGATTTCC ATCATCATCA AGGATCTGTG ATGAGGTGAT GTTGTCTGAG AGCTGTGTCA     120

GTGCGTCAGA GGACTGAGCC TGGGCAACTG GAGTGAACAC GGACAATGCC ACAGCGCTTG     180

CTGTAACAAG GGTCAAAGTA CTTCGACGCA AAGACAAAAC TTTTCTCCTG GCAATAAATA     240

TGCGGATTTA CTATGGAAAC AAGATAGAAG ATTGGATAGC GAAAGCTATC CTCAACTCGT     300

GGAAAGTGTA GTGCCACAAC CACAGTATTG GCTAGAAAAC AATCTATAGC ATTGTTCTAC     360

AAAGAGCTTG TTGGAAATAA AACCTATGCC AAAGTAGGTG CAATTCTAGG AGAAGATTAC     420

ACTAGTCAAC C ATG AGT GAA ACA TAC GTG TCT GAG AAA AGT CCA GGA GTG      470
             Met Ser Glu Thr Tyr Val Ser Glu Lys Ser Pro Gly Val
               1               5                  10

ATG GCT AGC GGA GCG GAG CTG ATT CGT GCC GCC GAC ATT CAA ACG GCG      518
Met Ala Ser Gly Ala Glu Leu Ile Arg Ala Ala Asp Ile Gln Thr Ala
     15                  20                  25

CAG GCA CGA ATT TCC TCC GTC ATT GCA CCA ACT CCA TTG CAG TAT TGC      566
Gln Ala Arg Ile Ser Ser Val Ile Ala Pro Thr Pro Leu Gln Tyr Cys
 30                  35                  40                  45

CCT CGT CTT TCT GAG GAA ACC GGA GCG GAA ATC TAC CTT AAG CGT GAG      614
Pro Arg Leu Ser Glu Glu Thr Gly Ala Glu Ile Tyr Leu Lys Arg Glu
                 50                  55                  60

GAT CTG CAG GAT GTT CGT TCC TAC AAG ATC CGC GGT GCG CTG AAC TCT      662
```

-continued

```
Asp Leu Gln Asp Val Arg Ser Tyr Lys Ile Arg Gly Ala Leu Asn Ser
             65                  70                  75

GGA GCG CAG TCA CCC CAA GAG CAG CGC GAT GCA GGT ATC GTT GCC GCA      710
Gly Ala Gln Ser Pro Gln Glu Gln Arg Asp Ala Gly Ile Val Ala Ala
         80                  85                  90

TCT GCA GGT AAC CAT GCC CAG GGC GTG GCC TAT GTG TGC AAG TCC TTG      758
Ser Ala Gly Asn His Ala Gln Gly Val Ala Tyr Val Cys Lys Ser Leu
     95                 100                 105

GGC GTT CAG GGA CGC ATC TAT GTT CCT GTG CAG ACT CCA AAG CAA AAG      806
Gly Val Gln Gly Arg Ile Tyr Val Pro Val Gln Thr Pro Lys Gln Lys
110                 115                 120                 125

CGT GAC CGC ATC ATG GTT CAC GGC GGA GAG TTT GTC TCC TTG GTG GTC      854
Arg Asp Arg Ile Met Val His Gly Gly Glu Phe Val Ser Leu Val Val
                130                 135                 140

ACT GGC AAT AAC TTC GAC GAA GCA TCG GCT GCA GCG CAT GAA GAT GCA      902
Thr Gly Asn Asn Phe Asp Glu Ala Ser Ala Ala Ala His Glu Asp Ala
            145                 150                 155

GAG CGC ACC GGC GCA ACG CTG ATC GAG CCT TTC GAT GCT CGC AAC ACC      950
Glu Arg Thr Gly Ala Thr Leu Ile Glu Pro Phe Asp Ala Arg Asn Thr
        160                 165                 170

GTC ATC GGT CAG GGC ACC GTG GCT GCT GAG ATC TTG TCG CAG CTG ACT      998
Val Ile Gly Gln Gly Thr Val Ala Ala Glu Ile Leu Ser Gln Leu Thr
    175                 180                 185

TCC ATG GGC AAG AGT GCA GAT CAC GTG ATG GTT CCA GTC GGC GGT GGC     1046
Ser Met Gly Lys Ser Ala Asp His Val Met Val Pro Val Gly Gly Gly
190                 195                 200                 205

GGA CTT CTT GCA GGT GTG GTC AGC TAC ATG GCT GAT ATG GCA CCT CGC     1094
Gly Leu Leu Ala Gly Val Val Ser Tyr Met Ala Asp Met Ala Pro Arg
                210                 215                 220

ACT GCG ATC GTT GGT ATC GAA CCA GCG GGA GCA GCA TCC ATG CAG GCT     1142
Thr Ala Ile Val Gly Ile Glu Pro Ala Gly Ala Ala Ser Met Gln Ala
            225                 230                 235

GCA TTG CAC AAT GGT GGA CCA ATC ACT TTG GAG ACT GTT GAT CCC TTT     1190
Ala Leu His Asn Gly Gly Pro Ile Thr Leu Glu Thr Val Asp Pro Phe
        240                 245                 250

GTG GAC GGC GGA GAG GTC AAA CGT GTC GGA GAT CTC AAC TAC ACC ATC     1238
Val Asp Gly Gly Glu Val Lys Arg Val Gly Asp Leu Asn Tyr Thr Ile
    255                 260                 265

GTG GAG AAG AAC CAG GGT CGC GTG CAC ATG ATG AGC GCG ACC GAG GGC     1286
Val Glu Lys Asn Gln Gly Arg Val His Met Met Ser Ala Thr Glu Gly
270                 275                 280                 285

GCT GTG TGT ACT GAG ATG CTC GAT CTT TAC CAA AAC GAA GGC ATC ATC     1334
Ala Val Cys Thr Glu Met Leu Asp Leu Tyr Gln Asn Glu Gly Ile Ile
                290                 295                 300

GCG GAG CCT GCT GGC GCG CTG TCT ATC GCT GGG TTG AAG GAA ATG TCC     1382
Ala Glu Pro Ala Gly Ala Leu Ser Ile Ala Gly Leu Lys Glu Met Ser
            305                 310                 315

TTT GCA CCT GGT TCT GTC GTG GTG TGC ATC ATC TCT GGT GGC AAC AAC     1430
Phe Ala Pro Gly Ser Val Val Val Cys Ile Ile Ser Gly Gly Asn Asn
        320                 325                 330

GAT GTG CTG CGT TAT GCG GAA ATC GCT GAG CGC TCC TTG GTG CAC CGC     1478
Asp Val Leu Arg Tyr Ala Glu Ile Ala Glu Arg Ser Leu Val His Arg
    335                 340                 345

GGT TTG AAG CAC TAC TTC TTG GTG AAC TTC CCG CAA AAG CCT GGT CAG     1526
Gly Leu Lys His Tyr Phe Leu Val Asn Phe Pro Gln Lys Pro Gly Gln
350                 355                 360                 365

TTG CGT CAC TTC CTG GAA GAT ATC CTG GGA CCG GAT GAT GAC ATC ACG     1574
Leu Arg His Phe Leu Glu Asp Ile Leu Gly Pro Asp Asp Asp Ile Thr
                370                 375                 380
```

-continued

```
CTG TTT GAG TAC CTC AAG CGC AAC AAC CGT GAG ACC GGT ACT GCG TTG     1622
Leu Phe Glu Tyr Leu Lys Arg Asn Asn Arg Glu Thr Gly Thr Ala Leu
            385                 390                 395

GTG GGT ATT CAC TTG AGT GAA GCA TCA GGA TTG GAT TCT TTG CTG GAA     1670
Val Gly Ile His Leu Ser Glu Ala Ser Gly Leu Asp Ser Leu Leu Glu
        400                 405                 410

CGT ATG GAG GAA TCG GCA ATT GAT TCC CGT CGC CTC GAG CCG GGC ACT     1718
Arg Met Glu Glu Ser Ala Ile Asp Ser Arg Arg Leu Glu Pro Gly Thr
    415                 420                 425

CCT GAG TAC GAA TAC TTG ACC TAAACATAGC TGAAGGCCAC CTCAATCGAG        1769
Pro Glu Tyr Glu Tyr Leu Thr
430                 435

GTGGCCTTTT TCTAGTTTCG GGTCAGGATC GCAAAGCCCC ACGGCTGAAG GGTTGTGGAG   1829

GTGTCGGTGA CGGTGGGGGA AGTGAAGCTG TAAATCAGCT CGCCGCCAAG CGGGACGGTG   1889

ATGGTGTCGT CGGAGAAATT CGCCAGAATT CGGCCG                             1925
```

(2) INFORMATION FOR SEQ ID NO:8:

(i) SEQUENCE CHARACTERISTICS:
(A) LENGTH: 436 amino acids
(B) TYPE: amino acid
(D) TOPOLOGY: linear (ii) MOLECULE TYPE: protein (xi) SEQUENCE DESCRIPTION: SEQ ID NO:8:

```
Met Ser Glu Thr Tyr Val Ser Glu Lys Ser Pro Gly Val Met Ala Ser
  1               5                  10                  15

Gly Ala Glu Leu Ile Arg Ala Ala Asp Ile Gln Thr Ala Gln Ala Arg
             20                  25                  30

Ile Ser Ser Val Ile Ala Pro Thr Pro Leu Gln Tyr Cys Pro Arg Leu
         35                  40                  45

Ser Glu Glu Thr Gly Ala Glu Ile Tyr Leu Lys Arg Glu Asp Leu Gln
     50                  55                  60

Asp Val Arg Ser Tyr Lys Ile Arg Gly Ala Leu Asn Ser Gly Ala Gln
 65                  70                  75                  80

Ser Pro Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240
```

-continued

```
Asn Gly Gly Pro Ile Thr Leu Glu Thr Val Asp Pro Phe Val Asp Gly
                245                 250                 255

Gly Glu Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

(2) INFORMATION FOR SEQ ID NO:9:

(i) SEQUENCE CHARACTERISTICS:
(A) LENGTH: 1925 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 432..1739

(xi) SEQUENCE DESCRIPTION: SEQ ID NO:9:

```
CGCCATTGCT GAGCATTGAG CTGCCTTCAG AGCTGCCTGG CCAGGTTTCG TTTCCATCGA     60

CTGGATTTCC ATCATCATCA AGGATCTGTG ATGAGGTGAT GTTGTCTGAG AGCTGTGTCA    120

GTGCGTCAGA GGACTGAGCC TGGGCAACTG GAGTGAACAC GGACAATGCC ACAGCGCTTG    180

CTGTAACAAG GGTCAAAGTA CTTCGACGCA AAGACAAAAC TTTTCTCCTG GCAATAAATA    240

TGCGGATTTA CTATGGAAAC AAGATAGAAG ATTGGATAGC GAAAGCTATC CTCAACTCGT    300

GGAAAGTGTA GTGCCACAAC CACAGTATTG GCTAGAAAAC AATCTATAGC ATTGTTCTAC    360

AAAGAGCTTG TTGGAAATAA AACCTATGCC AAAGTAGGTG CAATTCTAGG AGAAGATTAC    420

ACTAGTCAAC C ATG AGT GAA ACA TAC GTG TCT GAG AAA AGT CCA GGA GTG     470
             Met Ser Glu Thr Tyr Val Ser Glu Lys Ser Pro Gly Val
               1               5                  10

ATG GCT AGC GGA GCG GAG CTG ATT CGT GCC GCC GAC ATT CAA ACG GCG      518
Met Ala Ser Gly Ala Glu Leu Ile Arg Ala Ala Asp Ile Gln Thr Ala
     15                  20                  25

CAG GCA CGA ATT TCC TCC GTC ATT GCA CCA ACT CCA TTG CAG TAT TGC      566
```

-continued

```
Gln Ala Arg Ile Ser Ser Val Ile Ala Pro Thr Pro Leu Gln Tyr Cys
 30                 35                  40                  45

CCT CGT CTT TCT GAG GAA ACC GGA GCG GAA ATC TAC CTT AAG CGT GAG      614
Pro Arg Leu Ser Glu Glu Thr Gly Ala Glu Ile Tyr Leu Lys Arg Glu
                50                  55                  60

GAT CTG CAG GAT GTT CGT TCC TAC AAG ATC CGC GGT GCG CTG AAC TCT      662
Asp Leu Gln Asp Val Arg Ser Tyr Lys Ile Arg Gly Ala Leu Asn Ser
            65                  70                  75

GGA GCG CAG TCA CCC CAA GAG CAG CGC GAT GCA GGT ATC GTT GCC GCA      710
Gly Ala Gln Ser Pro Gln Glu Gln Arg Asp Ala Gly Ile Val Ala Ala
        80                  85                  90

TCT GCA GGT AAC CAT GCC CAG GGC GTG GCC TAT GTG TGC AAG TCC TTG      758
Ser Ala Gly Asn His Ala Gln Gly Val Ala Tyr Val Cys Lys Ser Leu
     95                 100                 105

GGC GTT CAG GGA CGC ATC TAT GTT CCT GTG CAG ACT CCA AAG CAA AAG      806
Gly Val Gln Gly Arg Ile Tyr Val Pro Val Gln Thr Pro Lys Gln Lys
110                 115                 120                 125

CGT GAC CGC ATC ATG GTT CAC GGC GGA GAG TTT GTC TCC TTG GTG GTC      854
Arg Asp Arg Ile Met Val His Gly Gly Glu Phe Val Ser Leu Val Val
                130                 135                 140

ACT GGC AAT AAC TTC GAC GAA GCA TCG GCT GCA GCG CAT GAA GAT GCA      902
Thr Gly Asn Asn Phe Asp Glu Ala Ser Ala Ala Ala His Glu Asp Ala
            145                 150                 155

GAG CGC ACC GGC GCA ACG CTG ATC GAG CCT TTC GAT GCT CGC AAC ACC      950
Glu Arg Thr Gly Ala Thr Leu Ile Glu Pro Phe Asp Ala Arg Asn Thr
        160                 165                 170

GTC ATC GGT CAG GGC ACC GTG GCT GCT GAG ATC TTG TCG CAG CTG ACT      998
Val Ile Gly Gln Gly Thr Val Ala Ala Glu Ile Leu Ser Gln Leu Thr
    175                 180                 185

TCC ATG GGC AAG AGT GCA GAT CAC GTG ATG GTT CCA GTC GGC GGT GGC     1046
Ser Met Gly Lys Ser Ala Asp His Val Met Val Pro Val Gly Gly Gly
190                 195                 200                 205

GGA CTT CTT GCA GGT GTG GTC AGC TAC ATG GCT GAT ATG GCA CCT CGC     1094
Gly Leu Leu Ala Gly Val Val Ser Tyr Met Ala Asp Met Ala Pro Arg
                210                 215                 220

ACT GCG ATC GTT GGT ATC GAA CCA GCG GGA GCA GCA TCC ATG CAG GCT     1142
Thr Ala Ile Val Gly Ile Glu Pro Ala Gly Ala Ala Ser Met Gln Ala
            225                 230                 235

GCA TTG CAC AAT GGT GGA CCA ATC ACT TTG GAG ACT GTT GAT CCC TTT     1190
Ala Leu His Asn Gly Gly Pro Ile Thr Leu Glu Thr Val Asp Pro Phe
        240                 245                 250

GTG GAC GGC GCA GAG GTC AAA CGT GTC GGA GAT CTC AAC TAC ACC ATC     1238
Val Asp Gly Ala Glu Val Lys Arg Val Gly Asp Leu Asn Tyr Thr Ile
    255                 260                 265

GTG GAG AAG AAC CAG GGT CGC GTG CAC ATG ATG AGC GCG ACC GAG GGC     1286
Val Glu Lys Asn Gln Gly Arg Val His Met Met Ser Ala Thr Glu Gly
270                 275                 280                 285

GCT GTG TGT ACT GAG ATG CTC GAT CTT TAC CAA AAC GAA GGC ATC ATC     1334
Ala Val Cys Thr Glu Met Leu Asp Leu Tyr Gln Asn Glu Gly Ile Ile
                290                 295                 300

GCG GAG CCT GCT GGC GCG CTG TCT ATC GCT GGG TTG AAG GAA ATG TCC     1382
Ala Glu Pro Ala Gly Ala Leu Ser Ile Ala Gly Leu Lys Glu Met Ser
            305                 310                 315

TTT GCA CCT GGT TCT GTC GTG GTG TGC ATC ATC TCT GGT GGC AAC AAC     1430
Phe Ala Pro Gly Ser Val Val Val Cys Ile Ile Ser Gly Gly Asn Asn
        320                 325                 330

GAT GTG CTG CGT TAT GCG GAA ATC GCT GAG CGC TCC TTG GTG CAC CGC     1478
Asp Val Leu Arg Tyr Ala Glu Ile Ala Glu Arg Ser Leu Val His Arg
    335                 340                 345
```

-continued

```
GGT TTG AAG CAC TAC TTC TTG GTG AAC TTC CCG CAA AAG CCT GGT CAG     1526
Gly Leu Lys His Tyr Phe Leu Val Asn Phe Pro Gln Lys Pro Gly Gln
350                 355                 360                 365

TTG CGT CAC TTC CTG GAA GAT ATC CTG GGA CCG GAT GAT GAC ATC ACG     1574
Leu Arg His Phe Leu Glu Asp Ile Leu Gly Pro Asp Asp Asp Ile Thr
                370                 375                 380

CTG TTT GAG TAC CTC AAG CGC AAC AAC CGT GAG ACC GGT ACT GCG TTG     1622
Leu Phe Glu Tyr Leu Lys Arg Asn Asn Arg Glu Thr Gly Thr Ala Leu
            385                 390                 395

GTG GGT ATT CAC TTG AGT GAA GCA TCA GGA TTG GAT TCT TTG CTG GAA     1670
Val Gly Ile His Leu Ser Glu Ala Ser Gly Leu Asp Ser Leu Leu Glu
        400                 405                 410

CGT ATG GAG GAA TCG GCA ATT GAT TCC CGT CGC CTC GAG CCG GGC ACT     1718
Arg Met Glu Glu Ser Ala Ile Asp Ser Arg Arg Leu Glu Pro Gly Thr
    415                 420                 425

CCT GAG TAC GAA TAC TTG ACC TAAACATAGC TGAAGGCCAC CTCAATCGAG        1769
Pro Glu Tyr Glu Tyr Leu Thr
430                 435

GTGGCCTTTT TCTAGTTTCG GGTCAGGATC GCAAAGCCCC ACGGCTGAAG GGTTGTGGAG   1829

GTGTCGGTGA CGGTGGGGGA AGTGAAGCTG TAAATCAGCT CGCCGCCAAG CGGGACGGTG   1889

ATGGTGTCGT CGGAGAAATT CGCCAGAATT CGGCCG                             1925
```

(2) INFORMATION FOR SEQ ID NO:10:

(i) SEQUENCE CHARACTERISTICS:
(A) LENGTH: 436 amino acids
(B) TYPE: amino acid
(D) TOPOLOGY: linear (ii) MOLECULE TYPE: protein (xi) SEQUENCE DESCRIPTION: SEQ ID NO:10:

```
Met Ser Glu Thr Tyr Val Ser Glu Lys Ser Pro Gly Val Met Ala Ser
  1               5                  10                  15

Gly Ala Glu Leu Ile Arg Ala Ala Asp Ile Gln Thr Ala Gln Ala Arg
             20                  25                  30

Ile Ser Ser Val Ile Ala Pro Thr Pro Leu Gln Tyr Cys Pro Arg Leu
         35                  40                  45

Ser Glu Glu Thr Gly Ala Glu Ile Tyr Leu Lys Arg Glu Asp Leu Gln
     50                  55                  60

Asp Val Arg Ser Tyr Lys Ile Arg Gly Ala Leu Asn Ser Gly Ala Gln
 65                  70                  75                  80

Ser Pro Gln Glu Gln Arg Asp Ala Gly Ile Val Ala Ala Ser Ala Gly
                 85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160

Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Gly Leu Leu
```

-continued

```
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Glu Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

(2) INFORMATION FOR SEQ ID NO:11:

(i) SEQUENCE CHARACTERISTICS:
(A) LENGTH: 1925 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 432..1739

(xi) SEQUENCE DESCRIPTION: SEQ ID NO:11:

```
CGCCATTGCT GAGCATTGAG CTGCCTTCAG AGCTGCCTGG CCAGGTTTCG TTTCCATCGA     60

CTGGATTTCC ATCATCATCA AGGATCTGTG ATGAGGTGAT GTTGTCTGAG AGCTGTGTCA    120

GTGCGTCAGA GGACTGAGCC TGGGCAACTG GAGTGAACAC GGACAATGCC ACAGCGCTTG    180

CTGTAACAAG GGTCAAAGTA CTTCGACGCA AAGACAAAAC TTTTCTCCTG GCAATAAATA    240

TGCGGATTTA CTATGGAAAC AAGATAGAAG ATTGGATAGC GAAAGCTATC CTCAACTCGT    300

GGAAAGTGTA GTGCCACAAC CACAGTATTG GCTAGAAAAC AATCTATAGC ATTGTTCTAC    360

AAAGAGCTTG TTGGAAATAA AACCTATGCC AAAGTAGGTG CAATTCTAGG AGAAGATTAC    420

ACTAGTCAAC C ATG AGT GAA ACA TAC GTG TCT GAG AAA AGT CCA GGA GTG     470
```

-continued

```
            Met Ser Glu Thr Tyr Val Ser Glu Lys Ser Pro Gly Val
              1               5                  10

ATG GCT AGC GGA GCG GAG CTG ATT CGT GCC GCC GAC ATT CAA ACG GCG      518
Met Ala Ser Gly Ala Glu Leu Ile Arg Ala Ala Asp Ile Gln Thr Ala
     15                  20                  25

CAG GCA CGA ATT TCC TCC GTC ATT GCA CCA ACT CCA TTG CAG TAT TGC      566
Gln Ala Arg Ile Ser Ser Val Ile Ala Pro Thr Pro Leu Gln Tyr Cys
 30                  35                  40                  45

CCT CGT CTT TCT GAG GAA ACC GGA GCG GAA ATC TAC CTT AAG CGT GAG      614
Pro Arg Leu Ser Glu Glu Thr Gly Ala Glu Ile Tyr Leu Lys Arg Glu
                 50                  55                  60

GAT CTG CAG GAT GTT CGT TCC TAC AAG ATC CGC GGT GCG CTG AAC TCT      662
Asp Leu Gln Asp Val Arg Ser Tyr Lys Ile Arg Gly Ala Leu Asn Ser
             65                  70                  75

GGA GCG CAG TCA CCC CAA GAG CAG CGC GAT GCA GGT ATC GTT GCC GCA      710
Gly Ala Gln Ser Pro Gln Glu Gln Arg Asp Ala Gly Ile Val Ala Ala
         80                  85                  90

TCT GCA GGT AAC CAT GCC CAG GGC GTG GCC TAT GTG TGC AAG TCC TTG      758
Ser Ala Gly Asn His Ala Gln Gly Val Ala Tyr Val Cys Lys Ser Leu
     95                 100                 105

GGC GTT CAG GGA CGC ATC TAT GTT CCT GTG CAG ACT CCA AAG CAA AAG      806
Gly Val Gln Gly Arg Ile Tyr Val Pro Val Gln Thr Pro Lys Gln Lys
110                 115                 120                 125

CGT GAC CGC ATC ATG GTT CAC GGC GGA GAG TTT GTC TCC TTG GTG GTC      854
Arg Asp Arg Ile Met Val His Gly Gly Glu Phe Val Ser Leu Val Val
                130                 135                 140

ACT GGC AAT AAC TTC GAC GAA GCA TCG GCT GCA GCG CAT GAA GAT GCA      902
Thr Gly Asn Asn Phe Asp Glu Ala Ser Ala Ala Ala His Glu Asp Ala
            145                 150                 155

GAG CGC ACC GGC GCA ACG CTG ATC GAG CCT TTC GAT GCT CGC AAC ACC      950
Glu Arg Thr Gly Ala Thr Leu Ile Glu Pro Phe Asp Ala Arg Asn Thr
        160                 165                 170

GTC ATC GGT CAG GGC ACC GTG GCT GCT GAG ATC TTG TCG CAG CTG ACT      998
Val Ile Gly Gln Gly Thr Val Ala Ala Glu Ile Leu Ser Gln Leu Thr
    175                 180                 185

TCC ATG GGC AAG AGT GCA GAT CAC GTG GTG GTT CCA GTC GGC GGT GGC     1046
Ser Met Gly Lys Ser Ala Asp His Val Val Val Pro Val Gly Gly Gly
190                 195                 200                 205

GGA CTT CTT GCA GGT GTG GTC AGC TAC ATG GCT GAT ATG GCA CCT CGC     1094
Gly Leu Leu Ala Gly Val Val Ser Tyr Met Ala Asp Met Ala Pro Arg
                210                 215                 220

ACT GCG ATC GTT GGT ATC GAA CCA GCG GGA GCA GCA TCC ATG CAG GCT     1142
Thr Ala Ile Val Gly Ile Glu Pro Ala Gly Ala Ala Ser Met Gln Ala
            225                 230                 235

GCA TTG CAC AAT GGT GGA CCA ATC ACT TTG GAG ACT GTT GAT CCC TTT     1190
Ala Leu His Asn Gly Gly Pro Ile Thr Leu Glu Thr Val Asp Pro Phe
        240                 245                 250

GTG GAC GGC GCA GAG GTC AAA CGT GTC GGA GAT CTC AAC TAC ACC ATC     1238
Val Asp Gly Ala Glu Val Lys Arg Val Gly Asp Leu Asn Tyr Thr Ile
    255                 260                 265

GTG GAG AAG AAC CAG GGT CGC GTG CGC ATG ATG AGC GCG ACC GAG GGC     1286
Val Glu Lys Asn Gln Gly Arg Val Arg Met Met Ser Ala Thr Glu Gly
270                 275                 280                 285

GCT GTG TGT ACT GAG ATG CTC GAT CTT TAC CAA AAC GAA GGC ATC ATC     1334
Ala Val Cys Thr Glu Met Leu Asp Leu Tyr Gln Asn Glu Gly Ile Ile
                290                 295                 300

GCG GAG CCT GCT GGC GCG CTG TCT ATC GCT GGG TTG AAG GAA ATG TCC     1382
Ala Glu Pro Ala Gly Ala Leu Ser Ile Ala Gly Leu Lys Glu Met Ser
            305                 310                 315
```

-continued

```
TTT GCA CCT GGT TCT GTC GTG GTG TGC ATC ATC TCT GGT GGC AAC AAC      1430
Phe Ala Pro Gly Ser Val Val Val Cys Ile Ile Ser Gly Gly Asn Asn
        320                 325                 330

GAT GTG CTG CGT TAT GCG GAA ATC GCT GAG CGC TCC TTG GTG CAC CGC      1478
Asp Val Leu Arg Tyr Ala Glu Ile Ala Glu Arg Ser Leu Val His Arg
    335                 340                 345

GGT TCG AAG CAC TAC TTC TTG GTG AAC TTC CCG CAA AAG CCT GGT CAG      1526
Gly Ser Lys His Tyr Phe Leu Val Asn Phe Pro Gln Lys Pro Gly Gln
350                 355                 360                 365

TTG CGT CAC TTC CTG GAA GAT ATC CTG GGA CCG GAT GAT GAC ATC ACG      1574
Leu Arg His Phe Leu Glu Asp Ile Leu Gly Pro Asp Asp Asp Ile Thr
                370                 375                 380

CTG TTT GAG TAC CTC AAG CGC AAC AAC CGT GAG ACC GGT ACT GCG TTG      1622
Leu Phe Glu Tyr Leu Lys Arg Asn Asn Arg Glu Thr Gly Thr Ala Leu
            385                 390                 395

GTG GGT ATT CAC TTG AGT GAA GCA TCA GGA TTG GAT TCT TTG CTG GAA      1670
Val Gly Ile His Leu Ser Glu Ala Ser Gly Leu Asp Ser Leu Leu Glu
        400                 405                 410

CGT ATG GAG GAA TCG GCA ATT GAT TCC CGT CGC CTC GAG CCG GGC ACT      1718
Arg Met Glu Glu Ser Ala Ile Asp Ser Arg Arg Leu Glu Pro Gly Thr
    415                 420                 425

CCT GAG TAC GAA TAC TTG ACC TAAACATAGC TGAAGGCCAC CTCAATCGAG         1769
Pro Glu Tyr Glu Tyr Leu Thr
430                 435

GTGGCCTTTT TCTAGTTTCG GGTCAGGATC GCAAAGCCCC ACGGCTGAAG GGTTGTGGAG    1829

GTGTCGGTGA CGGTGGGGGA AGTGAAGCTG TAAATCAGCT CGCCGCCAAG CGGGACGGTG    1889

ATGGTGTCGT CGGAGAAATT CGCCAGAATT CGGCCG                              1925
```

(2) INFORMATION FOR SEQ ID NO:12:

(i) SEQUENCE CHARACTERISTICS:
(A) LENGTH: 436 amino acids
(B) TYPE: amino acid
(D) TOPOLOGY: linear (ii) MOLECULE TYPE: protein (xi) SEQUENCE DESCRIPTION: SEQ ID NO:12:

```
Met Ser Glu Thr Tyr Val Ser Glu Lys Ser Pro Gly Val Met Ala Ser
  1               5                  10                  15

Gly Ala Glu Leu Ile Arg Ala Ala Asp Ile Gln Thr Ala Gln Ala Arg
            20                  25                  30

Ile Ser Ser Val Ile Ala Pro Thr Pro Leu Gln Tyr Cys Pro Arg Leu
        35                  40                  45

Ser Glu Glu Thr Gly Ala Glu Ile Tyr Leu Lys Arg Glu Asp Leu Gln
    50                  55                  60

Asp Val Arg Ser Tyr Lys Ile Arg Gly Ala Leu Asn Ser Gly Ala Gln
 65                  70                  75                  80

Ser Pro Gln Glu Gln Arg Asp Ala Gly Ile Val Ala Ala Ser Ala Gly
                85                  90                  95

Asn His Ala Gln Gly Val Ala Tyr Val Cys Lys Ser Leu Gly Val Gln
            100                 105                 110

Gly Arg Ile Tyr Val Pro Val Gln Thr Pro Lys Gln Lys Arg Asp Arg
        115                 120                 125

Ile Met Val His Gly Gly Glu Phe Val Ser Leu Val Val Thr Gly Asn
    130                 135                 140

Asn Phe Asp Glu Ala Ser Ala Ala Ala His Glu Asp Ala Glu Arg Thr
145                 150                 155                 160
```

-continued

```
Gly Ala Thr Leu Ile Glu Pro Phe Asp Ala Arg Asn Thr Val Ile Gly
                165                 170                 175

Gln Gly Thr Val Ala Ala Glu Ile Leu Ser Gln Leu Thr Ser Met Gly
            180                 185                 190

Lys Ser Ala Asp His Val Val Val Pro Val Gly Gly Gly Gly Leu Leu
        195                 200                 205

Ala Gly Val Val Ser Tyr Met Ala Asp Met Ala Pro Arg Thr Ala Ile
    210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Glu Val Lys Arg Val Gly Asp Leu Asn Tyr Thr Ile Val Glu Lys
            260                 265                 270

Asn Gln Gly Arg Val Arg Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Ser Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435
```

(2) INFORMATION FOR SEQ ID NO:13:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:13:

```
CGCAGCTGAC TTCCATGGGG CAAGA                                         25
```

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear -continued (ii) MOLECULE TYPE: other nucleic acid
(A) DESCRIPTION: /desc = "primer"

(xi) SEQUENCE DESCRIPTION: SEQ ID NO:14:

CGTACGTTCG AACCGTGACC 20

(2) INFORMATION FOR SEQ ID NO:15:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:15:

GGTCAGGGCA CCGTGGCTGC TG 22

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:16:

GGAGACTGTT GATCCCTTTG 20

(2) INFORMATION FOR SEQ ID NO:17:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:17:

CCTTTGCACC TGGTTCTGTC 20

(2) INFORMATION FOR SEQ ID NO:18:

(i) SEQUENCE CHARACTERISTICS:
(A) LENGTH: 22 base pairs
(B) TYPE: nucleic acid
(C) STRANDEDNESS: single
(D) TOPOLOGY: linear -continued

```
(ii) MOLECULE TYPE: other nucleic acid
      (A) DESCRIPTION: /desc = "primer"

(xi) SEQUENCE DESCRIPTION: SEQ ID NO:18:

CCTCAAGCGC AACAACCGTG AG                                        22
```

PRODUCTION OF L-ISOLEUCINE BY MEANS OF RECOMBINANT MICROORGANISMS WITH DEREGULATED THREONINE DEHYDRATASE

This application is a National Phase filing of PCT/DE95/00017, filed Jan. 9, 1995.

The invention relates to a method for the microbial production of L-isoleucine wherein a threonine dehydratase gene is altered so as to deregulate the feed back inhibition of L-isoleucine by threonine dehydratase. The invention also relates to a gene structure and vector corresponding to the altered threonine dehydratase gene. The invention also relates to a transformed cell which contains the aforementioned gene structure.

The amino acid L-isoleucine is essential for man and animals. It is widely used in dietetic foods and as a component of various nutrient mixtures for medicinal purposes. L-Isoleucine is also used as an additive or as a reagent in the pharmaceutical and chemical industries.

Microorganisms, which secrete L-isoleucine into a fermentation medium, are used to obtain this amino acid, which is formed by the biosynthetic path shown in FIG. 1. As is also demonstrated in FIG. 1, there are key enzymes in the biosynthesis of the L-isoleucine, namely aspartic acid kinase, homoserine dehydrogenase and threonine dehydratase. The activity of the aspartic acid kinase and of the homoserine dehydrogenase is inhibited by the feedback of the amino acid, L-threonine, which is also formed within the scope of the biosynthesis of the L-isoleucine, while the key enzyme, threonine dehydratase, which is specific for the synthesis of L-isoleucine, is inhibited by the feedback of the end product of the biosynthetic chain, L-isoleucine.

In the past, attempts have been made time and again to increase the formation of L-isoleucine by obtaining mutants of L-isoleucine producers which, relative to the wild types, form more L-isoleucine.

To obtain such mutants, mutagenesis was carried out exclusively in vivo, that is, a mutagen was allowed to act on the whole of the genome. Mutated microorganisms, the above-mentioned key enzymes of which no longer are subject to a feed-back inhibition, were selected on the basis of the resistance to amino acid analogs.

For example, a mutation, which leads to a resistance to α-aminobutyrate or isoleucine hydroxamate, is described in U.S. Pat. No. 4,329,427. According to this example, microorganisms admittedly produce increased amounts of isoleucine; however, the question as to which enzymes are no longer inhibited by feedback, is not clarified.

The U.S. Pat. No. 4,442,208 and 4,601,983 disclose that, after an in vivo mutagenesis, it was possible to isolate a DNA fragment, which is not defined more precisely and which brings about resistance to α-aminohydroxyvaleric acid. After this fragment is transferred to a Corynebacterium or a Brevibacterium strain, the latter produce increasing amounts of L-isoleucine.

Methods have also been described, for which, by means of oversynthesis of feedback-regulated key enzymes, L-isoleucine can be formed increasingly (see, for example, the German Offenlegungsschrift 3,942,947 and the European publication 0 137 348).

Overall, all previously described methods for increasing the L-isoleucine production have the common feature that mutations were more likely to lead randomly to deregulated key enzymes, which are no longer subject to feedback inhibition and that the amino acid synthesis was increased by these means.

It is an object of the invention to provide a method for the microbial production of L-isoleucine, by means of which defined mutations of the key enzyme of the L-isoleucine biosynthesis, the threonine dehydratase, is selectively changed so that feedback inhibition by L-isoleucine no longer takes place.

The objective, on which the invention is based, is accomplished owing to the fact that, in a gene of a threonine dehydratase, present in vitro, one or several bases are exchanged in such a manner by mutation in the region of the gene coding for the allosteric domains of the enzyme, that at least one amino acid in the amino acid sequence of the allosteric domains of the enzyme is replaced by a different one in such a manner, that the enzyme is no longer inhibited by L-isoleucine feedback. "A gene, present in vitro" in this case means that the threonine dehydratase gene is cloned, that is, isolated and incorporated in a vector, before mutagenesis. The mutagenesis by exchange of base(s) is accomplished by known methods, for example, by the method of Ito et al. (Gene 102 (1991) 67–70). After transformation of threonine dehydratase genes, so mutated, in a host cell producing threonine or L-isoleucine, the host cell increasingly produces L-isoleucine.

In principle, a cloned threonine dehydratase gene or one present in vitro can originate from any bacterium. Since Corynebacterium glutamicum is one of the "classical" amino acid producers, the gene preferably originates from this microorganism, particularly from the ATCC 13032 strain. The DNA sequence of the threonine dehydratase gene from this Corynebacterium glutamicum strain is already known (see Mockel et al., J. Bacteriol. 174 (1992) 8065–8072). After a base exchange in the gene region coding for the allosteric domains of the enzyme, the DNA sequences, listed in Tables 1 to 3, (SEQ. ID. Nos. 1, 3 & 5, respectively) are obtained for example. In the Tables, the gene region, coding for the allosteric domains of the enzymes, is underlined and the base exchange sites are indicated by additional underlining.

After the mutagenesis is carried out, the in vitro mutated genes are incorporated in a plasmid, in which the expression of the threonine dehydratase gene can be induced. As plasmids, pVC 19 or pKK 223-3, for example, are suitable (Amman et al., Gene 25, 167). After incorporation of the mutated genes in a suitable plasmid, they are transformed in a suitable bacterial strain.

In order to obtain those clones, which also actually contain the plasmids with the mutated threonine dehydratase genes, the transformants desired can be isolated by the usual method by way of the resistance of amino acid analogs, β-methylnorleucine, isoleucine hydroxamate or hydroxyisoleucine coming into consideration as analogs.

However, a simpler and more concerted isolation is attained owing to the fact that the changed threonine dehydratase genes are transformed in a microorganism, the acetohydroxy acid synthase activity of which can be inhibited by L-valine. *Escherichia coli* K 12 strains, preferably the strains JM109 of DH 5, are suitable as transformants. The transformants are subsequently brought onto a solid medium, which contains the L-isoleucine for inhibiting the threonine dehydratase and L-valine for inhibiting metabolization of the ketobutyrate by the acetohydroxy acid synthetase (Umbarger: *Escherichia coli* and *Salmonella typhimurium,* 1 (1987) 352–367). A substance for inducing the threonine dehydratase gene and L-threonine as substrate for the dehydratase are preferably added to the medium in addition. Preferably, IPTG (isopropyl-β-D-thiogalactopyranoside) is used as substance for inducing the threonine dehydratase gene, so that an IPTG-induceable promoter is connected in series with the altered threonine dehydratase gene in the vector. Such clones, which contain a deregulated threonine dehydratase, convert the L-threonine without inhibition into ketobutyrate. Since the further reaction of the ketobutyrate by acetohydroxy acid synthase is inhibited by the L-valine that has been added, the ketobutyrate accumulates. As a result, the clones, which contain a deregulated threonine dehydratase, do not grow as well because of the known toxicity of ketobutyrate (La Rossa and Schloss, J. Biol. Chem. 259 (1984) 8753–8757). The poorer growth is expressed by the formation of smaller colonies, more translucent colonies or colonies with a jagged outline. These colonies can easily be "abgeimpft" (inoculated off) and therefore clones with deregulated dehydratase can easily be isolated.

This method of isolating can, of course, also be used for those transformants, which contain a cloned threonine dehydratase gene, which has been modified by mutations other than base exchange, so that the corresponding enzyme no longer is subject to feedback inhibition.

An inventive alternative for accomplishing said objective consists therein that, in a gene of a threonine dehydratase from *Corynebacterium glutamicum* present in vitro, the amino acid alanine in position 257 of the amino acid sequence of the enzyme is replaced by the amino acid glycine (Table 4) (SEQ ID NO:8) or the amino acid methionine in position 199 of the amino acid sequence of the enzyme is replaced by the amino acid valine (Table 5) (SEQ ID NO:10) by a base exchange outside of the gene region coding for the allosteric domains of the enzyme. After transformation of the threonine dehydratase gene so mutated into a host cell producing threonine or L-isoleucine, the host cell increasingly forms L-isoleucine.

A further alternative for accomplishing the inventive objective consists therein that, in a threonine dehydratase gene from *Corynebacterium glutamicum,* the amino acid, histidine, in position 278 of the amino acid sequence of the enzyme is replaced by the amino acid arginine by base exchange outside of the gene region coding for the allosteric domains of the enzyme and the amino acid leucine in position 351 of the amino acid sequence of the enzyme is replaced by the amino acid serine (Table 6) (SEQ ID NO:12) by base exchange within the gene region coding for the allosteric domain of the enzyme. After transformation of the threonine dehydratase gene so mutated into a host cell producing threonine or L-isoleucine, this host cell also increasingly forms L-isoleucine.

Preferably *Corynebacterium glutamicum* and, particularly, the deposited DSM strain 8890 is suitable as host cell for the transformation of a mutated threonine dehydratase gene or as production strain. As transformants, the strains deposited with the DSM under the numbers 8889 and 8891, for example, are obtainable, which increasingly secrete L-isoleucine into the fermentation medium. It is also beneficial to use production strains or host cells for the transformation, which no longer synthesize the wild type threonine dehydratase, which is still regulated by L-isoleucine, so that only deregulated threonine dehydratase still catalyzes the conversion of L-threonine in the cells.

BRIEF DESCRIPTION OF THE DRAWINGS

FIG. 1 shows the biosynthetic pathway for L-isoleucine.

EXAMPLE

Figure 2:
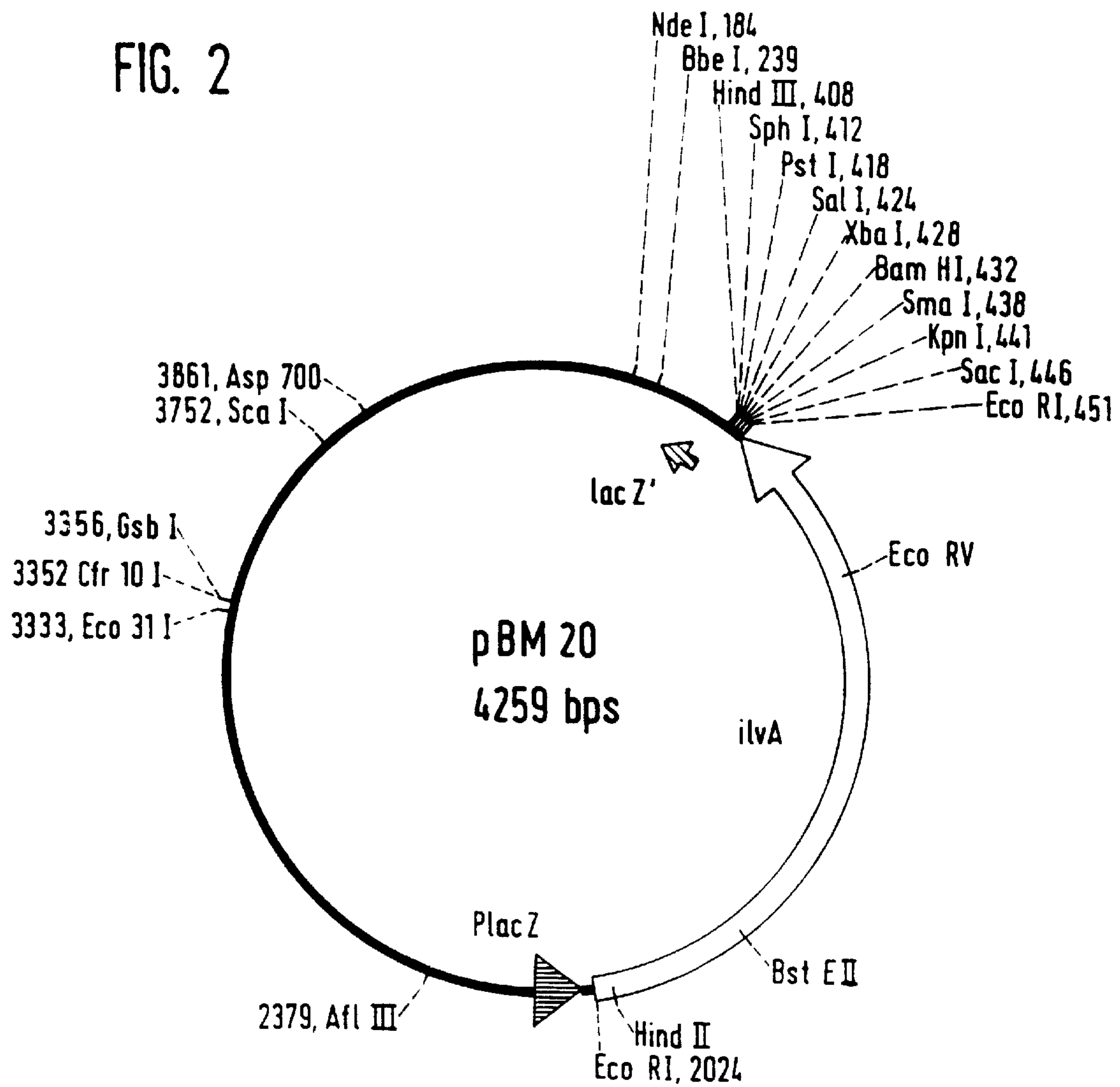
FIG. 2 shows a map of the plasmid pBM20.

1. Production of Mutated Enzymes, Which are no Longer Subject to Feedback Inhibition 1.1 Selection of the Desired Enzymes The known plasmid pBM1/Exo8, which codes the regulated threonine dehydratase of the wild type of *Corynebacterium glutamicum* (Möckel, et al., J. Bacteriol. 174 (1992) 8065–8072), was isolated by known methods (Sambrook et al., Molecular Cloning, A Laboratory Handbook, 1989, Cold Spring Harbor Laboratory Press). It was subsequently digested with the restriction enzyme EcoR1 and the fragment, containing the threonine dehydratase gene and consisting of 1573 base pairs, was isolated. This fragment was ligated in the EcoR1 cut site of the known vector pUC19 (Vieira and Messing, Gene 19 (1976) 259–268). By these means, the plasmid pBM20 was obtained (FIG. 2), in which the threonine dehydratase gene from *C. glutamicum,* which itself is not expressed in *E. coli,* (Cordes et al., Gene 112 (1992) 113–116), is present in the standard laboratory strain of *E. coli* JM109 under the control of the lacZ promoter of the original vector pUC19, which can be induced by isopropyl-D-thiogalactopyranoside.

In order to introduce non-directional mutations in the allosteric domains of the threonine dehydratase, two DNA primers (SEQ ID NOS 13 & NO:15) were synthesized by a known method in a separate procedure:

5'-primer: CGCAGCTGACTTCCATGGGGCAAGA

3'-primer: CCAGTGCCAAGCTTGCATGC

The 5' primer is homologous with the Ncol cut site (underlined) in the threonine dehydratase gene. The 3' primer is homologous with the HindIII recognition site (underlined) of the multiple cloning site of the output vector pUC19.

With both primers, a polymerase chain reaction was now carried out (Tindall and Kunkel, Biochemistry 27 (1988) 6008–6013), in which new DNA fragments, which contain mutations, result from the nonspecific reaction of the Taq polymerase (Leung et al., Technique 1 (1989) 11–15). In a final volume of 100 μL, the reaction formulation contained 20 μL of 5' primer (25 μg/mL), 20 μL of 3' primer (25 μg/mL), 1 ng of template (pBM20), 100 μM of ATP, 100 μM of dNTP mix, 10 μL Taq 10× buffer (100 mM of tris, 15 mM of $MgCl_2$, 500 mM of KCl, 1 mg/mL of gelatin, pH 8.3), 0.5 U of Taq polymerase (5 U/μL) and 0.5 mM of $MnCl_2$. The reaction conditions were set as follows: a time delay file of 94° C. (3 minutes), a thermo cycle file of 94° C. (1 minute), 55° C. (2 minutes), 72° C. (3 minutes), a soak file of 4° C., a segment extension of 10 seconds, the number of cycles being 30. After the reaction, the DNA fragments were purified (Sambrook et al., Molecular Cloning, A Laboratory Handbook, 1989, Cold Spring Harbor Laboratory Press), digested with Ncol and HindIII and ligated with pBM20, from which the corresponding 743 base pairs Ncol-HindIII fragment, which codes for the allosteric domains of the wild type threonine dehydratase, had previously been cut out.

With these in vitro produced ligation products, which also contain mutated threonine dehydratase genes, *E. coli* JM109 was now transformed by known methods (Hanahan, Techniques for Transformation of *E. coli* (1985) DNA Cloning, volume 1, pp. 109–136, IRL Press Oxford) and about 10,000 clones, containing plasmid, were obtained on Luria-Bertani medium (Lennox, Virology 1 (1955) 190–206), which contained 50 μg/mL of ampicillin.

In order to identify the clones, which code for a threonine dehydratase, which can no longer be inhibited by feedback, a Luria-Bertani medium was prepared, which additionally contained 40 mM of L-threonine as substrate for the threonine dehydratase, as well as 1 mM of isopropyl-β-D-thiogalactopyranoside for inducing the lacZ-induced expression of the threonine dehydratase gene. As is well known, the Luria-Bertani medium already contains sufficient L-valine for inhibiting the activity of the acetohydroxy acid synthase in *E. coli* (Umbarger, Biosynthesis of Branched-Chain Amino Acids (1987) *Escherichia coli* and *Salmonella typhimurium*, vol. 1, pp. 352–367, American Society for Microbiology, Washington, DC) in order to attain the highest possible accumulation of α-ketobutyrate by the method described here. Aside from the Luria-Bertani medium, which contained threonine and isopropyl-β-D-thiogalactopyranoside, the same medium was prepared as a control without isopropyl-β-D-thiogalactopyranoside, so that there was no induction of the threonine dehydratase. Subsequently, the clones of *E. coli* JM109, which contained the pBM20 derivatives to be tested, were stamped on these plates in the conventional manner and incubated for 24 hours at 37° C. After that, it was possible to identify on the medium, which contained isopropyl-β-D-thiogalactopyranoside 60 abnormally growing colonies, which were distinguished by a lesser growth or paler colonies or colonies having a jagged edge, but grew normally on the control medium without isopropyl-β-D-thiogalactopyranoside. These clones were subjected individually to an identical follow-up test and, subsequently, 6 of the clones with a pronounced growth retardation were subjected to a biochemical test for characterizing the regulation of the threonine dehydratases containing them.

1.2 Characterizing the Inhibition of the Enzymes

Six of the recombinant clones of *E. coli* JM109, so obtained, were inoculated in 100 mL of LB liquid medium, which additionally contained 50 μg of ampicillin/mL and incubated at 37° C. The optical density ($OD_{600}$ nm) was followed. When the OD reached a value of 0.5, the isopropyl-β-D-thiogalactopyranoside was added until it reached a final concentration of 0.5 mM. After incubating for a further hour at 37° C., the cells were harvested by centrifuging, washed once with a pH 7.0 buffer (0.1 M potassium phosphate, 0.5 mM L-isoleucine, 0.2 mM pyridoxal phosphate) and taken up in 1 mL of the same buffer and disintegrated by an ultrasonic treatment in the Branson-Sonifier W250 (3 minutes, pulsed with an interval of 20% and an output of 2). For separating the cell fragments, the homogenate was centrifuged for 10 minutes at 13,000 rpm and 4° C. in a Sigma refrigerated centrifuge. Subsequently, the resulting clear supernatant (crude extract) was used in the enzyme test for determining threonine dehydratase activity and regulation.

In a final volume of 0.8 mL, the enzyme test contained 0.1 M potassium phosphate (pH 8.2), 1 mM of pyridoxal phosphate, 40 mM of L-threonine and crude extract. The mixture was incubated at 30° C. and 200 μL samples were taken after 0 and 30 minutes. The threonine dehydratase reaction was terminated in each case by the addition of 1 mL of reagent. This consisted of 1 g of semicarbazide plus 0.9 g of sodium acetate in 100 mL of water. After incubating for 15 minutes at 30° C., 3 mL of water were added and the extinction was determined at 254 nm in a Zeiss PM6 spectrophotometer. Controls and calibration values with 0 to 1.5 μmoles of ketobutyrate were treated identically and the amount of ketobutyrate, actually formed in the enzyme test by the threonine dehydratase, was determined from a calibration curve. Parallel to this, identical formulations were carried out, which contained 5 mM of L-isoleucine for testing for the inhibition of threonine dehydratase. Independently of this determination, the protein content of the crude extracts was determined as described (Bradford, Anal. Biochem. 72 (1976) 248–254). The specific activities obtained and the degree of inhibition are evident from Table 7.

TABLE 7

Characterization of Mutated Threonine Dehydratases and the Ability to Inhibit Them by L-Isoleucine

| Clone | Specific Activity of Threonine Dehydratase (μmoles/min/mg of Protein) –Ile | +5 mM Ile |
|---|---|---|
| wild type | 1.561 | 0.240 |
| 28 | 1.771 | 1.907 |
| 16 | 0.412 | 0.251 |
| 31 | 1.932 | 0.590 |
| 50 | 0.220 | 0.132 |
| 54 | 0.28 | 0.136 |
| 14 | 1.708 | 1.989 |

It can be seen directly that the mutated enzymes 38 and 14 are not inhibited allosterically by L-isoleucine. In the presence of L-isoleucine, the enzyme of mutant 31 still has 30% of the activity, whereas the enzyme of the wild type has only 15% of the activity under these conditions.

1.3 Characterization of the Mutation Site of the Enzyme

To determine the mutations in the enzymes produced, the plasmids, coding for threonine dehydratase, were isolated from *E. coli* JM109 clones by standard methods. The sequencing of the mutated region of the threonine dehydratase gene was carried out with the help of the didesoxynucleotide termination method of Sanger et al. (Sanger et al., Proceedings of the National Academy of Sciences, U.S.A. (1977) 5463–5467). Fluorescein-labeled sequence-specific nucleotides were synthesized as primers following the directions of Pharmacia (Pharmacia, Uppsala, Sweden). These primers were purified by means of high-pressure liquid chromatography with a gradient of 5–30% acetonitrile in 100 mM of triethylamine acetate of pH 7.0 and 5 μm of the Pharmacia SuperPac® Pep-S. The primers were used in a standard sequencing reaction and, during the electrophoresis, the reaction products were identified by fluorescence detection on the A. L. F. sequencer (Pharmacia, Uppsala, Sweden) and detected automatically and the resulting sequence was recorded.

Primers Used for the Sequencing

Figure 3:
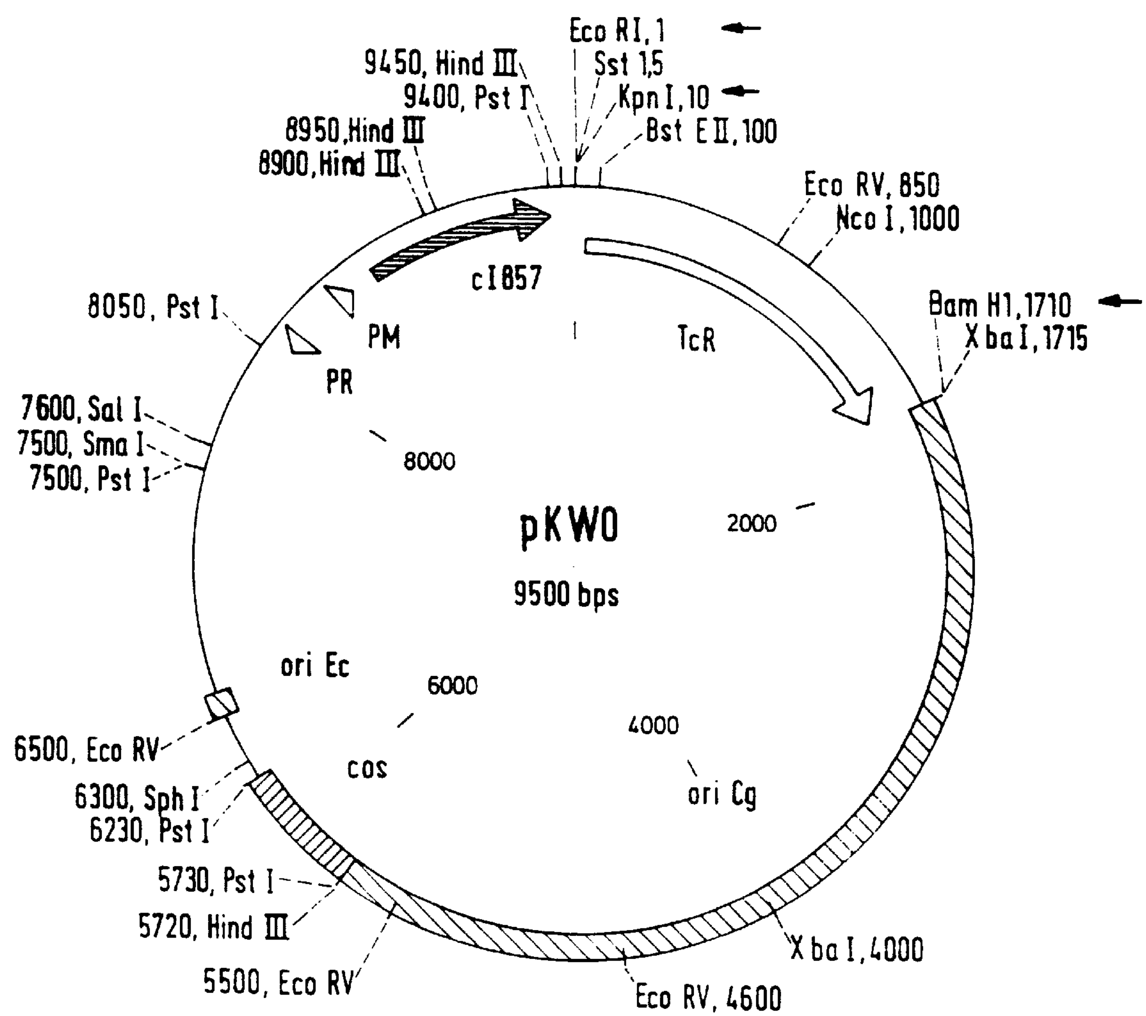
FIG. 3 shows a map of the plasmid pKW0.

The position of the bases refers to the sequence in FIG. 3 in Möckel et al., J. Bacteriol. 174 (1992) 8065–8072.

Base 957–958(SEQ ID NO:15): 5'-Fluorescein-d (GGTCAGGGCACCGTGGCTGCTG)-3'

Base 1172–1191 (SEQ ID NO:16): 5'-Fluorescein-d (GGAGACTGTTGATCCCTTTG)-3'

Base 1381–1400 (SEQ ID NO:17): 5'-Fluorescein-d (CCTTTGCACCTGGTTCTGTC)-3'

Base 1586–1607 (SEQ ID NO:18): 5'-Fluorescein-d (CCTCAAGCGCAACAACCGTGAG)-3'

The sequence of the individual threonine dehydratase genes, determined this manner, was compared with the known sequence of the wild type (Möckel et J. Bacteriol. 174 (1992) 8065–8072). The individual base exchanges of the biochemically characterized threonine dehydratase genes are given in Table 8. The altered codons were translated into the corresponding amino acids by means of the universal genetic code and the amino acid exchanges, which were thus detected and lead to altered regulation of the threonine dehydratase, are also listed in Table 8. Mutations with a deregulated phenotype were obtained over the whole of the region used for the mutation. In mutant 14, there is a double mutation, which shows that several exchanges of amino acids in one enzyme can also lead to the desired deregulated phenotype.

TABLE 8

Genetic Characterization of Threonine Dehydratase with Altered Allosteric Regulation

| | Nucleotide Exchange | | | Amino Acid Exchange | | |
|---|---|---|---|---|---|---|
| Mutants | Position | Wild Type | Mutants | Position | Wild Type | Mutants |
| 38 | 1398 | GTC | GCC | 323 | Val | Ala |
| 16 | 1559 | GAT | GGT | 377 | Asp | Gly |
| 31 | 1579 | TTT | TGT | 383 | Phe | Cys |
| 50 | 1200 | GCA | GGA | 257 | Ala | Gly |
| 54 | 1026 | ATG | GTG | 199 | Met | Val |
| 14 | 1264 | CAC | CGC | 278 | His | Arg |
| | 1483 | TTG | TCG | 351 | Leu | Ser |

2. Determination of the Isoleucine Secretion by Deregulated Enzymes

The alleles obtained were recloned in *E. coli/C. glutamicum* shuttle vectors, in order to be able to express them in this manner in a threonine producer of *C. glutamicum.*

For this purpose, the *E. coli/C. glutamicum* shuttle vector pKWO was produced to begin with by known cloning methods (Sambrook et al., Molecular Cloning, A Laboratory Handbook, 1989, Cold Spring Harbor Laboratory Press). The resulting vector of 9.5 kb is shown in FIG. 1. It contains (i) the *C. glutamicum* replicon pGA2 (Sonnen, Molekulargenetische Charakterisierung von Phagen-Wirt-Beziehungen bei coryneformen Aminosaure-Produzenten (Molecular Genetic Characterization of Phage-Host Relationships in the Case of Coryneform Amino Acid Producers), dissertation, Technical University of Darmstadt, 1991), which leads to only a low number of copies in *C. glutamicum,* (ii) the *E. coli* replicon from pOU71 (Larsen et al., Gene 28 (1984) 45–54), which leads to one copy per cell at 30° C. and up to 1000 copies per cell at 42° C., (iii) the tetracycline resistance from pHY163 (Ishiwa and Shibahara, Jpn. J. Genet 60 (1985) 485–498) and (iv) the cos site from pBTI-1 (Boehringer, Mannheim). The ilvA alleles 14, 16 and 18, as well as the wild type allele, were isolated as EcoRI fragments from pBM20 derivatives, produced under 1.1, and ligated with the EcoRI-restrung vector pKWO, in order to result in pKWOilvA, pKWOilvA14, pKWOilvA16, pKWOilvA38. With these plasmids, the threonine producer MH20-22B::pSUR5-DR1 (Reinscheid et al., Appl. Env. Microbiol. (1994), in press) was transformed by means of electroporation (Liebl et al., FEMS Microbiol. Lett. 65 (1985) 299–304). MH20-22B has been filed with the Deutschen Sammlung fir Mikroorganismen (German Collection for Microorganisms) under the number DSM 6870, as were MH20-22B::pSUR5-DR1 (DSM 8890) and MH20-22B::pSUR5-DR1 pKWOilvA16 (DSM 8889). These strains were cultured in the minimum medium CGXII as described (Keilhauer et al., J. Bacteriol. 175 (1993) 5595–5603), and the amino acids, which had accumulated in the culture medium after a 72-hour incubation, were determined. Table 9 clearly shows that the formation of L-isoleucine is increased by the mutant alleles.

TABLE 9

Effect of the Expression of the Alleles of the Mutants 38, 14 and 16 on the Production of Amino Acid with *G. glutamicum*

| Strain | Thr | Lys (mM) | Ile |
|---|---|---|---|
| MH20-22B | 0 | 76 | 1 |
| MH20-22B::pSUR5-DR1 | 36 | 26 | 16 |
| MH20-22B::pSUR5-DR1 pKWOilvA | 14 | 26 | 40 |
| MH20-22B::pSUR5-DR1 pKWOiivA14 | 0 | 24 | 55 |
| MH20-22B::pSUR5-DR1 pKWOilvA16 | 0 | 22 | 50 |
| MH20-22B::pSUR5-DR1 pKWOilvA38 | 0 | 20 | 53 |

In a further experiment, the wild type allele and the allele of mutant 38 were incorporated in the high copy pendulum vector pECM3 (A. Schäfer, Diploma Thesis, 1991, University of Bielefeld). The fragments once again were isolated as EcoRI fragments from the pBM20 derivatives produced under 1.1 and ligated with the EcoRI-restrung vector, in order to result in pECM3ilvA and pECM3ilvA38. With these plasmids, the threonine producer MH20-22B::pSUR5-DR1 (Reinscheid et al., Appl. Env. Microbiol. (1994), in press) was transformed by means of electroporation (Liebl et al., FEMS Microbiol. Lett. 65 (1985) 299–304). MH20-22B has been filed with the Deutschen Sammlung fur Mikroorganismen (German Collection for Microorganisms) under the number DSM 6870, as were MH20-22B::pSUR5-DR1 (DSM 8890) and MH20-22B::pSUR5-DR1 pECM3ilvA38 (DSM 8891). These strains were cultured in the MH20-22B minimum medium, as described (Schrumpf et al. Appl. Microbiol. Biotechnol. 37 (1992) 566–571) and the amino acids, which had accumulated in the culture medium after a 72-hour incubation, were determined. Table 10 once again clearly shows that the formation of L-isoleucine is increased by the respective mutant allele.

TABLE 10

Effect of the Expression of the Alleles of Mutant 38 on the Production of Amino Acid with C. glutamicum

| Strain | Thr | Lys (mM) | Ile |
|---|---|---|---|
| MH20-22B | 0 | 158 | 2 |
| MH20-22B::pSUR5-DR1 | 53 | 61 | 29 |
| MH20-22B::pSUR5-DR1 pECM3i1vA | 0 | 55 | 88 |
| MH20-22B::pSUR5-DR1 pECM3i1vA38 | 0 | 59 | 125 |

TABLE 1

Mutant 38 (SEQ ID NO:1)

```
          .         .         .         .         .
CGCCATTGCTGAGCATTGAGCTGCCTTCAGAGCTGCCTGGCCAGGTTTCG

          .         .         .         .         .
TTTCCATCGACTGGATTTCCATCATCATCAAGGATCTGTGATGAGGTGAT     100

          .         .         .         .         .
GTTGTCTGAGAGCTGTGTCAGTGCGTCAGAGGACTGAGCCTGGGCAACTG

          .         .         .         .         .
GAGTGAACACGGACAATGCCACAGCGCTTGCTGTAACAAGGGTCAAAGTA     200

          .         .         .         .         .
CTTCGACGCAAAGACAAAACTTTTCTCCTGGCAATAAATATGCGGATTTA

          .         .         .         .         .
CTATGGAAACAAGATAGAAGATTGGATAGCGAAAGCTATCCTCAACTCGT     300

          .         .         .         .         .
GGAAAGTGTAGTGCCACAACCACAGTATTGGCTAGAAAACAATCTATAGC

          .         .         .         .         .
ATTGTTCTACAAAGAGCTTGTTGGAAATAAAACCTATGCCAAAGTAGGTG     400

          .         .    HindII          .         .
CAATTCTAGGAGAAGATTACACTAGTCAACCATGAGTGAAACATACGTGT
                                 M  S  I  T  Y  V

          .         .         .         .         .
CTGAGAAAAGTCCAGGAGTGATGGCTAGCGGAGCGGAGCTGATTCGTGCC     500
S  I  N  S  P  G  V  M  A  S  G  A  I  I  I  P  A       23

          .         .         .         .         .
GCCGACATTCAAACGGCGCAGGCACGAATTTCCTCCGTCATTGCACCAAC
 A  D  I  Q  I  A  Q  A  R  I  S  S  V  I  A  P  T

          .         .         .         .         .
TCCATTGCAGTATTGCCCTCGTCTTTCTGAGGAAACCGGAGCGGAAATCT     600
 P  L  Q  Y  C  P  R  I  S  I  F  I  G  A  I  I         56

          .         .         .         .         .
ACCTTAAGCGTGAGGATCTGCAGGATGTTCGTTCCTACAAGATCCGCGGT
Y  L  K  R  E  D  L  Q  D  V  R  S  Y  K  I  R  G

          .         .         .         .         .
GCGCTGAACTCTGGAGCGCAGTCACCCCAAGAGCAGCGCGATGCAGGTAT     700
 A  L  N  S  G  A  Q  S  P  V  E  Q  R  D  A  C  I      90

          .    BstEII          .         .         .
CGTTGCCGCATCTGCAGGTAACCATGCCCAGGGCGTGGCCTATGYGTGCA
 V  A  A  S  A  G  N  H  A  Q  G  V  A  Y  V  C

          .         .         .         .         .
AGTCCTTGGGCGTTCAGGGACGCATCTATGTTCCTGTGCAGACTCCAAAG     800
K  S  L  G  V  Q  G  R  I  Y  V  P  V  Q  T  P  N     123

          .         .         .         .         .
CAAAAGCGTGACCGCATCATGGTTCACGGCGGAGAGTTTGTCTCCTTGGT
 Q  K  R  D  R  I  M  V  H  G  G  E  F  V  S  L  V

          .         .         .         .         .
GGTCACTGGCAATAACTTCGACGAAGCATCGGCTGCAGCGCATGAAGATG     900
 V  T  G  N  N  F  D  E  A  S  A  A  A  N  E  D        156

          .         .         .         .         .
CAGAGCGCACCGGCGCAACGCTGATCGAGCCTTTCGATGCTCGCAACACC
A  E  R  T  G  A  T  L  I  E  P  F  D  A  R  N  T

          .         .    BglII     .         .
GTCATCGGTCAGGGCACCGTGGCTGCTGAGATCTTGTCGCAGCTGACTTC    1000
 V  I  G  Q  G  T  V  A  A  E  I  L  S  Q  L  T  S     190

          .         .         .         .         .
CATGGGCAAGAGTGCAGATCACGTGATGGTTCCAGTCGGCGGTGGCGGAC
 M  G  K  S  A  D  H  V  M  V  P  V  G  G  G  G

          .         .         .         .         .
```

TABLE 1-continued

Mutant 38 (SEQ ID NO:1)

```
TTCTTGCAGGTGTGGTCAGCTACATGGCTGATATGGCACCTCGCACTGCG   1100
L  L  A  G  V  V  S  Y  M  A  D  M  A  P  R  I  A     223

         .         .         .         .         .
ATCGTTGGTATCGAACCAGCGGGAGCAGCATCCATGCAGGCTGCATTGCA
 I  V  G  I  E  P  A  G  A  A  S  M  Q  A  A  L  H

         .         .         .         .         .
CAATGGTGGACCAATCACTTTGGAGACTGTTGATCCCTTTGTGGACGGCG   1200
 N  G  G  P  I  T  L  E  T  V  D  P  F  V  D  G       256

         .      BglII      .         .         .
CAGAGGTCAAACGTGTCGGAGATCTCAACTACACCATCGTGGAGAAGAAC
A  E  V  K  R  V  G  D  L  N  Y  T  I  V  E  K  N

         .         .         .         .         .
CAGGGTCGCGTGCACATGATGAGCGCGACCGAGGGCGCTGTGTGTACTGA   1300
 Q  G  R  V  H  M  M  S  A  T  E  G  A  V  C  T  C   290

         .         .         .         .         .
GATGCTCGATCTTTACCAAAACGAAGGCATCATCGCGGAGCCTGCTGGCG
  M  L  D  L  Y  Q  N  E  G  I  I  A  E  P  A  G

         .         .         .         .         .
CGCTGTCTATCGCTGGGTTGAAGGAAATGTCCTTTGCACCTGGTTCTGCC   1400
A  L  S  I  A  G  L  K  E  M  S  F  A  P  G  S  A    323
                                   ---------------

         .         .         .         .         .
GTGGTGTGCATCATCTCTGGTGGCAACAACGATGTGCTGCGTTATGCGGA
 V  V  C  I  I  S  G  G  N  N  D  V  L  R  Y  A  E
--------------------------------------------------

         .         .         .         .         .
AATCGCTGAGCGCTCCTTGGTGCACCGCGGTTTGAAGCACTACTTCTTGG   1500
  I  A  E  R  S  L  V  H  R  G  L  K  H  Y  I  L     356
--------------------------------------------------

         .         .         .         .   EcoRV.
TGAACTTCCCGCAAAAGCCTGGTCAGTTGCGTCACTTCCTGGAAGATATC
V  N  F  P  Q  K  P  G  Q  L  R  H  F  L  E  D  I
--------------------------------------------------

         .         .         .         .         .
CTGGGACCGGATGATGACATCACGCTGTTTGAGTACCTCAAGCGCAACAA   1600
L  G  P  D  D  D  I  T  L  F  E  Y  L  K  R  H  N    390
--------------------------------------------------

         .         .         .         .         .
CCGTGAGACCGGTACTGCGTTGGTGGGTATTCACTTGAGTGAAGCATCAG
 R  E  T  G  T  A  L  V  G  I  H  L  S  E  A  S
--------------------------------------------------

         .         .         .         .         .
GATTGGATTCTTTGCTGGAACGTATGGAGGAATCGGCAATTGATTCCCGT   1700
G  L  D  S  L  L  E  R  M  E  E  S  A  I  D  S  R    423
--------------------------------------------------

         .         .         .         .         .
CGCCTCGAGCCGGGCACTCCTGAGTACGAATACTTGACCTAAACATAGCT
 R  L  E  P  G  T  P  E  Y  E  Y  L  T  *
---------------------------------------

         .         .         .         .         .
GAAGGCCACCTCAATCGAGGTGGCCTTTTTCTAGTTTCGGGTCAGGATCG   1800
                                                      436

         .         .         .         .         .
CAAAGCCCCACGGCTGAAGGGTTGTGGAGGTGTCGGTGACGGTGGGGGAA

         .         .         .         .         .
GTGAAGCTGTAAATCAGCTCGCCGCCAAGCGGGACGGTGATGGTGTCGTC   1900

         .    EcoRI     .
GGAGAAATTCGCCAGAATTCGGCCG
```

TABLE 2

Mutant 16 (SEQ ID NO:3)

```
CGCCATTGCTGAGCATTGAGCTGCCTTCAGAGCTGCCTGGCCAGGTTTCG

TTTCCATCGACTGGATTTCCATCATCATCAAGGATCTGTGATGAGGTGAT       100

GTTGTCTGAGAGCTGTGTCAGTGCGTCAGAGGACTGAGCCTGGGCAACTG

GAGTGAACACGGACAATGCCACAGCGCTTGCTGTAACAAGGGTCAAAGTA       200

CTTCGACGCAAAGACAAAACTTTTCTCCTGGCAATAAATATGCGGATTTA

CTATGGAAACAAGATAGAAGATTGGATAGCGAAAGCTATCCTCAACTCGT       300

GGAAAGTGTAGTGCCACAACCACAGTATTGGCTAGAAAACAATCTATAGC

ATTGTTCTACAAAGAGCTTGTTGGAAATAAAACCTATGCCAAAGTAGGTG       400

                     HindII
CAATTCTAGGAGAAGATTACACTAGTCAACCATGAGTGAAACATACGTGT
                                M  S  E  T  Y  V

CTGAGAAAAGTCCAGGAGTGATGGCTAGCGGAGCGGAGCTGATTCGTGCC       500
S  E  K  S  P  G  V  M  A  S  G  A  I  I  I  R  A         23

GCCGACATTCAAACGGCGCAGGCACGAATTTCCTCCGTCATTGCACCAAC
 A  D  I  Q  I  A  Q  A  R  I  S  S  V  I  A  P  T

TCCATTGCAGTATTGCCCTCGTCTTTCTGAGGAAACCGGAGCGGAAATCT       600
 P  L  Q  Y  C  P  R  L  S  C  E  T  G  A  E  I           56

ACCTTAAGCGTGAGGATCTGCAGGATGTTCGTTCCTACAAGATCCGCGGT
Y  L  K  R  E  D  L  Q  D  V  R  S  Y  K  I  R  G

GCGCTGAACTCTGGAGCGCAGTCACCCCAAGAGCAGCGCGATGCAGGTAT       700
 A  L  N  S  G  A  Q  S  P  Q  E  Q  P  Q  A  G  I         90

             BstEII
CGTTGCCGCATCTGCAGGTAACCATGCCCAGGGCGTGGCCTATGTGTGCA
 V  A  A  S  A  G  N  H  A  Q  G  V  A  Y  V  C

AGTCCTTGGGCGTTCAGGGACGCATCTATGTTCCTGTGCAGACTCCAAAG       800
K  S  L  G  V  Q  G  R  I  Y  V  P  V  Q  T  P  K        123

CAAAAGCGTGACCGCATCATGGTTCACGGCGGAGAGTTTGTCTCCTTGGT
 Q  K  R  D  R  I  M  V  H  G  G  E  F  V  S  L  V

GGTCACTGGCAATAACTTCGACGAAGCATCGGCTGCAGCGCATGAAGATG       900
 V  T  G  N  N  F  D  E  A  S  A  A  A  H  E  D          156

CAGAGCGCACCGGCGCAACGCTGATCGAGCCTTTCGATGCTCGCAACACC
A  E  R  T  G  A  T  L  I  E  P  F  D  A  R  N  T

                                BglII
GTCATCGGTCAGGGCACCGTGGCTGCTGAGATCTTGTCGCAGCTGACTTC      1000
 V  I  G  Q  G  T  V  A  A  E  I  L  S  Q  L  T  S       190

CATGGGCAAGAGTGCAGATCACGTGATGGTTCCAGTCGGCGGTGGCGGAC
 M  G  K  S  A  D  H  V  M  V  P  V  G  G  G  G
```

TABLE 2-continued

Mutant 16 (SEQ ID NO:3)

```
TTCTTGCAGGTGTGGTCAGCTACATGGCTGATATGGCACCTCGCACTGCG      1100
L  L  A  G  V  V  S  Y  M  A  D  M  A  P  R  T  A        223

         .         .         .         .         .
ATCGTTGGTATCGAACCAGCGGGAGCAGCATCCATGCAGGCTGCATTGCA
 I  V  G  I  E  P  A  G  A  A  S  M  Q  A  A  L  H

         .         .         .         .         .
CAATGGTGGACCAATCACTTTGGAGACTGTTGATCCCTTTGTGGACGGCG      1200
 N  G  G  P  I  T  L  E  T  V  D  P  F  V  D  G          256

         .        BglII      .         .         .
CAGAGGTCAAACGTGTCGGAGATCTCAACTACACCATCGTGGAGAAGAAC
A  E  V  K  R  V  G  D  L  N  Y  T  I  V  E  K  N

         .         .         .         .         .
CAGGGTCGCGTGCACATGATGAGCGCGACCGAGGGCGCTGTGTGTACTGA      1300
 Q  G  R  V  H  M  M  S  A  T  E  G  A  V  C  T  E       290

         .         .         .         .         .
GATGCTCGATCTTTACCAAAACGAAGGCATCATCGCGGAGCCTGCTGGCG
  M  L  D  L  Y  Q  N  E  G  I  I  A  E  P  A  G

         .         .         .         .         .
CGCTGTCTATCGCTGGGTTGAAGGAAATGTCCTTTGCACCTGGTTCTGTC      1400
A  L  S  I  A  G  L  K  E  M  S  F  A  P  G  S  V        323
                                       ---------------

         .         .         .         .         .
GTGGTGTGCATCATCTCTGGTGGCAACAACGATGTGCTGCGTTATGCGGA
 V  V  C  I  I  S  G  G  N  N  D  V  L  R  Y  A  E
--------------------------------------------------

         .         .         .         .         .
AATCGCTGAGCGCTCCTTGGTGCACCGCGGTTTGAAGCACTACTTCTTGG      1500
  I  A  E  R  S  L  V  H  R  G  L  K  H  Y  F  L        356
--------------------------------------------------

           .         .         .         .    EcoR
TGAACTTCCCGCAAAAGCCTGGTCAGTTGCGTCACTTCCTGGAAGATATC
V  N  F  P  Q  K  P  G  Q  L  R  H  F  L  E  D  I
--------------------------------------------------

V.         .         .         .         .
CTGGGACCGGGTGATGACATCACGCTGTTTGAGTACCTCAAGCGCAACAA      1600
 L  G  P  G  D  D  I  T  L  F  E  Y  L  K  R  H  N       390
--------------------------------------------------

         .         .         .         .         .
CCGTGAGACCGGTACTGCGTTGGTGGGTATTCACTTGAGTGAAGCATCAG
  R  E  T  G  T  A  L  V  G  I  H  L  S  E  A  S
--------------------------------------------------

         .         .         .         .         .
GATTGGATTCTTTGCTGGAACGTATGGAGGAATCGGCAATTGATTCCCGT      1700
G  L  D  S  L  L  E  R  M  E  E  S  A  I  D  S  R        423
--------------------------------------------------

         .         .         .         .         .
CGCCTCGAGCCGGGCACTCCTGAGTACGAATACTTGACCTAAACATAGCT
 R  L  E  P  G  T  P  E  Y  E  Y  L  T  *
---------------------------------------

         .         .         .         .         .
GAAGGCCACCTCAATCGAGGTGGCCTTTTTCTAGTTTCGGGTCAGGATCG      1800
                                                         436

         .         .         .         .         .
CAAAGCCCCACGGCTGAAGGGTTGTGGAGGTGTCGGTGACGGTGGGGGAA

         .         .         .         .         .
GTGAAGCTGTAAATCAGCTCGCCGCCAAGCGGGACGGTGATGGTGTCGTC      1900

         .    EcoRI     .
GGAGAAATTCGCCAGAATTCGGCCG
```

TABLE 3

Mutant 31 (SEQ ID NO:5)

```
         .         .         .         .         .
CGCCATTGCTGAGCATTGAGCTGCCTTCAGAGCTGCCTGGCCAGGTTTCG

         .         .         .         .         .
TTTCCATCGACTGGATTTCCATCATCATCAAGGATCTGTGATGAGGTGAT     100

         .         .         .         .         .
GTTGTCTGAGAGCTGTGTCAGTGCGTCAGAGGACTGAGCCTGGGCAACTG

         .         .         .         .         .
GAGTGAACACGGACAATGCCACAGCGCTTGCTGTAACAAGGGTCAAAGTA     200

         .         .         .         .         .
CTTCGACGCAAAGACAAAACTTTTCTCCTGGCAATAAATATGCGGATTTA

         .         .         .         .         .
CTATGGAAACAAGATAGAAGATTGGATAGCGAAAGCTATCCTCAACTCGT     300

         .         .         .         .         .
GGAAAGTGTAGTGCCACAACCACAGTATTGGCTAGAAAACAATCTATAGC

         .         .         .         .         .
ATTGTTCTACAAAGAGCTTGTTGGAAATAAAACCTATGCCAAAGTAGGTG     400

         .         .   HindII            .         .
CAATTCTAGGAGAAGATTACACTAGTCAACCATGAGTGAAACATACGTGT
                                M  S  E  T  Y  V

         .         .         .         .         .
CTGAGAAAAGTCCAGGAGTGATGGCTAGCGGAGCGGAGCTGATTCGTGCC     500
S  E  K  S  P  G  V  M  A  S  G  A  E  I  I  R  A       23

         .         .         .         .         .
GCCGACATTCAAACGGCGCAGGCACGAATTTCCTCCGTCATTGCACCAAC
 A  D  I  Q  T  A  Q  A  R  I  S  S  V  I  A  P  T

         .         .         .         .         .
TCCATTGCAGTATTGCCCTCGTCTTTCTGAGGAAACCGGAGCGGAAATCT     600
  P  L  Q  Y  C  P  R  L  S  C  E  T  G  A  E  I        56

         .         .         .         .         .
ACCTTAAGCGTGAGGATCTGCAGGATGTTCGTTCCTACAAGATCCGCGGT
Y  L  K  R  E  D  L  Q  D  V  R  S  Y  K  I  R  G

         .         .         .         .         .
GCGCTGAACTCTGGAGCGCAGTCACCCCAAGAGCAGCGCGATGCAGGTAT     700
A  L  N  S  G  A  Q  S  P  Q  E  Q  R  D  A  G  I       90

         .      BstEII       .         .         .
CGTTGCCGCATCTGCAGGTAACCATGCCCAGGGCGTGGCCTATGTGTGCA
  V  A  A  S  A  G  N  H  A  Q  G  V  A  Y  V  C

         .         .         .         .         .
AGTCCTTGGGCGTTCAGGGACGCATCTATGTTCCTGTGCAGACTCCAAAG     800
K  S  L  G  V  Q  G  R  I  Y  V  P  V  Q  T  P  K      123

         .         .         .         .         .
CAAAAGCGTGACCGCATCATGGTTCACGGCGGAGAGTTTGTCTCCTTGGT
 Q  K  R  D  R  I  M  V  H  G  G  E  F  V  S  L  V

         .         .         .         .         .
GGTCACTGGCAATAACTTCGACGAAGCATCGGCTGCAGCGCATGAAGATG     900
  V  T  G  N  N  F  D  E  A  S  A  A  A  H  E  D       156

         .         .         .         .         .
CAGAGCGCACCGGCGCAACGCTGATCGAGCCTTTCGATGCTCGCAACACC
A  E  R  T  G  A  T  L  I  E  P  F  D  A  R  N  T

         .         .          BglII      .         .
GTCATCGGTCAGGGCACCGTGGCTGCTGAGATCTTGTCGCAGCTGACTTC    1000
 V  I  G  Q  G  T  V  A  A  E  I  L  S  Q  L  T  S     190

         .         .         .         .         .
CATGGGCAAGAGTGCAGATCACGTGATGGTTCCAGTCGGCGGTGGCGGAC
  M  G  K  S  A  D  N  V  M  V  P  V  G  G  G  G

         .         .         .         .         .
```

TABLE 3-continued

Mutant 31 (SEQ ID NO:5)

```
TTCTTGCAGGTGTGGTCAGCTACATGGCTGATATGGCACCTCGCACTGCG   1100
L  L  A  G  V  V  S  Y  M  A  D  M  A  P  R  T  A     223

          .         .         .         .         .
ATCGTTGGTATCGAACCAGCGGGAGCAGCATCCATGCAGGCTGCATTGCA
 I  V  G  I  E  P  A  G  A  A  S  H  Q  A  A  L  H

          .         .         .         .         .
CAATGGTGGACCAATCACTTTGGAGACTGTTGATCCCTTTGTGGACGGCG   1200
 N  G  G  P  I  T  L  E  T  V  D  P  F  V  D  G       256

          .       BglII       .         .         .
CAGAGGTCAAACGTGTCGGAGATCTCAACTACACCATCGTGGAGAAGAAC
A  E  V  K  R  V  G  D  L  N  Y  T  I  V  E  K  N

          .         .         .         .         .
CAGGGTCGCGTGCACATGATGAGCGCGACCGAGGGCGCTGTGTGTACTGA   1300
 Q  G  R  V  H  M  M  S  A  T  E  G  A  V  C  T  E    290

          .         .         .         .         .
GATGCTCGATCTTTACCAAAACGAAGGCATCATCGCGGAGCCTGCTGCCG
  M  L  D  L  Y  Q  R  E  G  I  I  A  E  P  A  G

          .         .         .         .         .
CGCTGTCTATCGCTGGGTTGAAGGAAATGTCCTTTGCACCTGGTTCTGTC   1400
A  L  S  I  A  G  L  K  E  M  S  F  A  P  G  S  V     323
                                   --------------

          .         .         .         .         .
GTGGTGTGCATCATCTCTGGTGGCAACAACGATGTGCTGCGTTATGCGGA
 V  V  C  I  I  S  G  G  N  N  Q  V  L  R  Y  A  E
--------------------------------------------------

          .         .         .         .         .
AATCGCTGAGCGCTCCTTGGTGCACCGCGGTTTGAAGCACTACTTCTTGG   1500
  I  A  E  R  S  L  V  H  R  G  L  K  H  Y  F  L      356
--------------------------------------------------

          .         .         .         .  EcoRV.
TGAACTTCCCGCAAAAGCCTGGTCAGTTGCGTCACTTCCTGGAAGATATC
V  N  F  P  Q  K  P  G  Q  L  R  H  F  L  E  D  I
--------------------------------------------------

          .         .         .         .         .
CTGGGACCGGATGATGACATCACGCTGTGTGAGTACCTCAAGCGCAACAA   1600
 L  G  P  D  D  D  I  T  L  C  E  Y  L  K  R  N  N    390
--------------------------------------------------

          .         .         .         .         .
CCGTGAGACCGGTACTGCGTTGGTGGGTATTCACTTGAGTGAAGCATCAG
  R  E  T  G  T  A  L  V  G  I  H  L  S  E  A  S
--------------------------------------------------

          .         .         .         .         .
GATTGGATTCTTTGCTGGAACGTATGGAGGAATCGGCAATTGATTCCCGT   1700
G  L  D  S  L  L  E  R  M  E  E  S  A  I  D  S  A     423
--------------------------------------------------

          .         .         .         .         .
CGCCTCGAGCCGGGCACTCCTGAGTACGAATACTTGACCTAAACATAGCT
 R  L  E  P  G  T  P  C  Y  E  Y  L  T  *
---------------------------------------

          .         .         .         .         .
GAAGGCCACCTCAATCGAGGTGGCCTTTTTCTAGTTTCGGGTCAGGATCG   1800
                                                      436

          .         .         .         .         .
CAAAGCCCCACGGCTGAAGGGTTGTGGAGGTGTCGGTGACGGTGGGGGAA

          .         .         .         .         .
GTGAAGCTGTAAATCAGCTCGCCGCCAAGCGGGACGGTGATGGTGTCGTC   1900

          .    EcoRI    .
GGAGAAATTCGCCAGAATTCGGCCG
```

TABLE 4

Mutant 50 (SEQ ID NO:4)

```
CGCCATTGCTGAGCATTGAGCTGCCTTCAGAGCTGCCTGGCCAGGTTTCG

TTTCCATCGACTGGATTTCCATCATCATCAAGGATCTGTGATGAGGTGAT   100

GTTGTCTGAGAGCTGTGTCAGTGCGTCAGAGGACTGAGCCTGGGCAACTG

GAGTGAACACGGACAATGCCACAGCGCTTGCTGTAACAAGGGTCAAAGTA   200

CTTCGACGCAAAGACAAAACTTTTCTCCTGGCAATAAATATGCGGATTTA

CTATGGAAACAAGATAGAAGATTGGATAGCGAAAGCTATCCTCAACTCGT   300

GGAAAGTGTAGTGCCACAACCACAGTATTGGCTAGAAAACAATCTATAGC

ATTGTTCTACAAAGAGCTTGTTGGAAATAAAACCTATGCCAAAGTAGGTG   400

                         HindII
CAATTCTAGGAGAAGATTACACTAGTCAACCATGAGTGAAACATACGTGT
                                  M  S  I  T  Y  V

CTGAGAAAAGTCCAGGAGTGATGGCTAGCGGAGCGGAGCTGATTCGTGCC   500
S  E  K  S  P  G  V  M  A  S  G  A  E  I  I  H  A     23

GCCGACATTCAAACGGCGCAGGCACGAATTTCCTCCGTCATTGCACCAAC
 A  D  I  G  I  A  Q  A  R  I  S  S  V  I  A  P  T

TCCATTGCAGTATTGCCCTCGTCTTTCTGAGGAAACCGGAGCGGAAATCT   600
  P  L  Q  Y  C  P  R  L  S  I  I  T  G  A  I  I       56

ACCTTAAGCGTGAGGATCTGCAGGATGTTCGTTCCTACAAGATCCGCGGT
Y  L  K  R  E  D  L  Q  D  V  R  S  Y  K  I  R  G

GCGCTGAACTCTGGAGCGCAGTCACCCCAAGAGCAGCGCGATGCAGGTAT   700
 A  L  N  S  G  A  Q  S  P  Q  I  Q  F  D  A  G  I    90

               BstEII
CGTTGCCGCATCTGCAGGTAACCATGCCCAGGGCGTGGCCTATGTGTGCA
  V  A  A  S  A  G  H  H  A  Q  G  V  A  Y  V  C

AGTCCTTGGGCGTTCAGGGACGCATCTATGTTCCTGTGCAGACTCCAAAG   800
K  S  L  G  V  Q  G  R  I  Y  V  P  V  Q  T  P  K    123

CAAAAGCGTGACCGCATCATGGTTCACGGCGGAGAGTTTGTCTCCTTGGT
 Q  K  R  D  R  I  M  V  H  G  G  E  F  V  S  L  V

GGTCACTGGCAATAACTTCGACGAAGCATCGGCTGCAGCGCATGAAGATG   900
  V  T  G  N  N  F  D  E  A  S  A  A  A  H  E  D     156

CAGAGCGCACCGGCGCAACGCTGATCGAGCCTTTCGATGCTCGCAACACC
A  E  R  T  G  A  T  L  I  E  P  F  D  A  R  N  T

GTCATCGGTCAGGGCACCGTGGCTGCTGAGATCTTGTCGCAGCTGACTTC  1000
 V  I  G  Q  G  T  V  A  A  E  I  L  S  Q  L  T  S    190

CATGGGCAAGAGTGCAGATCACGTGATGGTTCCAGTCGGCGGTGGCGGAC
  M  G  K  S  A  D  H  V  M  V  P  V  G  G  G  G
```

TABLE 4-continued

Mutant 50 (SEQ ID NO:4)

```
TTCTTGCAGGTGTGGTCAGCTACATGGCTGATATGGCACCTCGCACTGCG  1100
L  L  A  G  V  V  S  Y  M  A  D  M  A  P  R  T  A   223

          .         .         .         .         .
ATCGTTGGTATCGAACCAGCGGGAGCAGCATCCATGCAGGCTGCATTGCA
 I  V  G  I  E  P  A  G  A  A  S  M  Q  A  A  L  H

          .         .         .         .         .
CAATGGTGGACCAATCACTTTGGAGACTGTTGATCCCTTTGTGGACGGCG  1200
  N  G  G  P  I  T  L  E  T  V  D  P  F  V  D  G     256

          .       BglII       .         .         .
GAGAGGTCAAACGTGTCGGAGATCTCAACTACACCATCGTGGAGAAGAAC
G  E  V  K  R  V  G  D  L  N  Y  T  I  V  E  K  N

          .         .         .         .         .
CAGGGTCGCGTGCACATGATGAGCGCGACCGAGGGCGCTGTGTGTACTGA  1300
 Q  G  R  V  H  M  M  S  A  T  C  G  A  V  C  T  E   290

          .         .         .         .         .
GATGCTCGATCTTTACCAAAACGAAGGCATCATCGCGGAGCCTGCTGGCG
  M  L  D  L  Y  Q  N  E  G  I  I  A  E  P  A  G

          .         .         .         .         .
CGCTGTCTATCGCTGGGTTGAAGGAAATGTCCTTTGCACCTGGTTCTGTC  1400
A  L  S  I  A  G  L  K  E  M  S  F  A  P  G  S  V   323
                                    --------------

          .         .         .         .         .
GTGGTGTGCATCATCTCTGGTGGCAACAACGATGTGCTGCGTTATGCGGA
 V  V  C  I  I  S  G  G  N  N  D  V  L  R  Y  A  E
--------------------------------------------------

          .         .         .         .         .
AATCGCTGAGCGCTCCTTGGTGCACCGCGGTTTGAAGCACTACTTCTTGG  1500
  I  A  E  R  S  L  V  H  R  G  L  K  H  Y  F  L     356
--------------------------------------------------

          .         .         .         .   EcoRV.
TGAACTTCCCGCAAAAGCCTGGTCAGTTGCGTCACTTCCTGGAAGATATC
V  N  F  P  Q  K  P  G  Q  L  R  H  F  L  E  D  I
--------------------------------------------------

          .         .         .         .         .
CTGGGACCGGATGATGACATCACGCTGTTTGAGTACCTCAAGCGCAACAA  1600
 L  G  P  D  D  D  I  T  L  F  E  Y  L  K  R  N  H   390
--------------------------------------------------

          .         .         .         .         .
CCGTGAGACCGGTACTGCGTTGGTGGGTATTCACTTCAGTGAAGCATCAG
  R  E  T  G  T  A  L  V  G  I  H  L  S  E  A  S
--------------------------------------------------

          .         .         .         .         .
GATTGGATTCTTTGCTGGAACGTATGGAGGAATCGGCAATTGATTCCCGT  1700
G  L  D  S  L  L  E  R  M  E  E  S  A  I  D  S  R   423
--------------------------------------------------

          .         .         .         .         .
CGCCTCGAGCCGGGCACTCCTGAGTACGAATACTTGACCTAAACATAGCT
 R  L  C  P  G  T  P  E  Y  C  Y  L  T  *
---------------------------------------

          .         .         .         .         .
GAAGGCCACCTCAATCGAGGTGGCCTTTTTCTAGTTTCGGGTCAGGATCG  1800
                                                    436

          .         .         .         .         .
CAAAGCCCCACGGCTGAAGGGTTGTGGAGGTGTCGGTGACGGTGGGGGAA

          .         .         .         .         .
GTGAAGCTGTAAATCAGCTCGCCGCCAAGCGGGACGGTGATGGTGTCGTC  1900

         .    EcoRI     .
GGAGAAATTCGCCAGAATTCGGCCG
```

TABLE 5

Mutant 54 (SEQ ID NO:10)

```
         .         .         .         .         .
CGCCATTGCTGAGCATTGAGCTGCCTTCAGAGCTGCCTGGCCAGGTTTCG

         .         .         .         .         .
TTTCCATCGACTGGATTTCCATCATCATCAAGGATCTGTGATGAGGTGAT    100

         .         .         .         .         .
GTTGTCTGAGAGCTGTGTCAGTGCGTCAGAGGACTGAGCCTGGGCAACTG

         .         .         .         .         .
GAGTGAACACGGACAATGCCACAGCGCTTGCTGTAACAAGGGTCAAAGTA    200

         .         .         .         .         .
CTTCGACGCAAAGACAAAACTTTTCTCCTGGCAATAAATATGCGGATTTA

         .         .         .         .         .
CTATGGAAACAAGATAGAAGATTGGATAGCGAAAGCTATCCTCAACTCGT    300

         .         .         .         .         .
GGAAAGTGTAGTGCCACAACCACAGTATTGGCTAGAAAACAATCTATAGC

         .         .         .         .         .
ATTGTTCTACAAAGAGCTTGTTGGAAATAAAACCTATGCCAAAGTAGGTG    400

         .         .   HindII          .         .
CAATTCTAGGAGAAGATTACACTAGTCAACCATGAGTGAAACATACGTGT
                                M  S  E  T  Y  V

         .         .         .         .         .
CTGAGAAAAGTCCAGGAGTGATGGCTAGCGGAGCGGAGCTGATTCGTGCC    500
S  F  F  S  P  G  V  M  A  S  G  A  I  I  I  R  A      23

         .         .         .         .         .
GCCGACATTCAAACGGCGCAGGCACGAATTTCCTCCGTCATTGCACCAAC
 A  D  I  Q  I  A  Q  A  R  I  S  S  V  I  A  P  T

         .         .         .         .         .
TCCATTGCAGTATTGCCCTCGTCTTTCTGAGGAAACCGGAGCGGAAATCT    600
 P  L  Q  Y  C  P  R  I  S  I  I  T  G  A  I  I        56

         .         .         .         .         .
ACCTTAAGCGTGAGGATCTGCAGGATGTTCGTTCCTACAAGATCCGCGGT
Y  I  K  R  E  D  L  Q  D  V  R  S  Y  K  I  R  G

         .         .         .         .         .
GCGCTGAACTCTGGAGCGCAGTCACCCCAAGAGCAGCGCGATGCAGGTAT    700
 A  L  N  S  G  A  Q  S  P  Q  T  Q  K  D  A  G  I     90

         .    BstEII           .         .         .
CGTTGCCGCATCTGCAGGTAACCATGCCCAGGGCGTGGCCTATGTGTGCA
 V  A  A  S  A  G  N  H  A  Q  G  V  A  Y  V  C

         .         .         .         .         .
AGTCCTTGGGCGTTCAGGGACGCATCTATGTTCCTGTGCAGACTCCAAAG    800
K  S  L  G  V  Q  G  T  I  Y  V  P  V  Q  T  P  K     123

         .         .         .         .         .
CAAAAGCGTGACCGCATCATGGTTCACGGCGGAGAGTTTGTCTCCTTGGT
 Q  K  R  D  R  I  M  V  H  G  G  E  F  V  S  L  V

         .         .         .         .         .
GGTCACTGGCAATAACTTCGACGAAGCATCGGCTGCAGCGCATGAAGATG    900
 V  T  G  H  N  F  D  E  A  S  A  A  A  H  E  D       156

         .         .         .         .         .
CAGAGCGCACCGGCGCAACGCTGATCGAGCCTTTCGATGCTCGCAACACC
A  E  R  T  G  A  T  L  I  E  P  F  D  A  R  N  T

         .         .       BglII       .         .
GTCATCGGTCAGGGCACCGTGGCTGCTGAGATCTTGTCGCAGCTGACTTC   1000
 V  I  G  Q  G  T  V  A  A  E  I  L  S  Q  L  T  S    190

         .         .         .         .         .
CATGGGCAAGAGTGCAGATCACGTGGTGGTTCCAGTCGGCGGTGGCGGAC
 M  G  K  S  A  D  H  V  V  V  P  V  G  G  G  G

         .         .         .         .         .
```

TABLE 5-continued

Mutant 54 (SEQ ID NO:10)

```
TTCTTGCAGGTGTGGTCAGCTACATGGCTGATATGGCACCTCGCACTGCG   1100
L  L  A  G  V  V  S  Y  M  A  D  M  A  P  R  T  A     223

         .         .         .         .         .
ATCGTTGGTATCGAACCAGCGGGAGCAGCATCCATGCAGGCTGCATTGCA
 I  V  G  I  E  P  A  G  A  A  S  M  Q  A  A  L  H

         .         .         .         .         .
CAATGGTGGACCAATCACTTTGGAGACTGTTGATCCCTTTGTGGACGGCG   1200
  N  G  G  P  I  T  L  E  T  V  D  P  F  V  D  G      256

         .       BglII     .         .         .
CAGAGGTCAAACGTGTCGGAGATCTCAACTACACCATCGTGGAGAAGAAC
A  E  V  K  R  V  G  D  L  H  Y  T  I  V  E  K  N

         .         .         .         .         .
CAGGGTCGCGTGCACATGATGAGCGCGACCGAGGGCGCTGTGTGTACTGA   1300
 Q  G  R  V  H  M  M  S  A  T  E  G  A  V  C  T  E    290

         .         .         .         .         .
GATGCTCGATCTTTACCAAAACGAAGGCATCATCGCGGAGCCTGCTGGCG
  M  L  D  L  Y  Q  N  E  G  I  I  A  E  P  A  G

         .         .         .         .         .
CGCTGTCTATCGCTGGGTTGAAGGAAATGTCCTTTGCACCTGGTTCTGTC   1400
A  L  S  I  A  G  L  K  E  M  S  F  A  P  G  S  V     323
                                   ---------------

         .         .         .         .         .
GTGGTGTGCATCATCTCTGGTGGCAACAACGATGTGCTGCGTTATGCGGA
 V  V  C  I  I  S  G  G  N  N  D  V  L  R  Y  A  E
--------------------------------------------------

         .         .         .         .         .
AATCGCTGAGCGCTCCTTGGTGCACCGCGGTTTGAAGCACTACTTCTTGG   1500
  I  A  E  R  S  L  V  H  R  G  L  K  H  Y  F  L      356
--------------------------------------------------

         .         .         .         .  EcoRV.
TGAACTTCCCGCAAAAGCCTGGTCAGTTGCGTCACTTCCTGGAAGATATC
V  H  F  P  Q  K  P  G  Q  L  R  H  F  L  E  D  I
--------------------------------------------------

         .         .         .         .         .
CTGGGACCGGATGATGACATCACGCTGTTTGAGTACCTCAAGCGCAACAA   1600
 L  G  P  D  D  D  I  I  L  F  E  Y  L  K  R  N  N    390
--------------------------------------------------

         .         .         .         .         .
CCGTGAGACCGGTACTGCGTTGGTGGGTATTCACTTGAGTGAAGCATCAG
  R  E  T  G  T  A  L  V  G  I  H  L  S  E  A  S
--------------------------------------------------

         .         .         .         .         .
GATTGGATTCTTTGCTGGAACGTATGGAGGAATCGGCAATTGATTCCCGT   1700
G  L  D  S  L  L  E  R  M  E  E  S  A  I  D  S  R     423
--------------------------------------------------

         .         .         .         .         .
CGCCTCGAGCCGGGCACTCCTGAGTACGAATACTTGACCTAAACATAGCT
 R  L  E  P  G  T  P  C  Y  E  Y  L  T  *
---------------------------------------

         .         .         .         .         .
GAAGGCCACCTCAATCGAGGTGGCCTTTTTCTAGTTTCGGGTCAGGATCG   1800
                                                      436

         .         .         .         .         .
CAAAGCCCCACGGCTGAAGGGTTGTGGAGGTGTCGGTGACGGTGGGGGAA

         .         .         .         .         .
GTGAAGCTGTAAATCAGCTCGCCGCCAAGCGGGACGGTGATGGTGTCGTC   1900

         .    EcoRI     .
GGAGAAATTCGCCAGAATTCGGCCG
```

TABLE 6

Mutant 14 (SEQ ID NO:12)

```
         .         .         .         .         .
CGCCATTGCTGAGCATTGAGCTGCCTTCAGAGCTGCCTGGCCAGGTTTCG

         .         .         .         .         .
TTTCCATCGACTGGATTTCCATCATCATCAAGGATCTGTGATGAGGTGAT      100

         .         .         .         .         .
GTTGTCTGAGAGCTGTGTCAGTGCGTCAGAGGACTGAGCCTGGGCAACTG

         .         .         .         .         .
GAGTGAACACGGACAATGCCACAGCGCTTGCTGTAACAAGGGTCAAAGTA      200

         .         .         .         .         .
CTTCGACGCAAAGACAAAACTTTTCTCCTGGCAATAAATATGCGGATTTA

         .         .         .         .         .
CTATGGAAACAAGATAGAAGATTGGATAGCGAAAGCTATCCTCAACTCGT      300

         .         .         .         .         .
GGAAAGTGTAGTGCCACAACCACAGTATTGGCTAGAAAACAATCTATAGC

         .         .         .         .         .
ATTGTTCTACAAAGAGCTTGTTGGAAATAAAACCTATGCCAAAGTAGGTG      400

         .         .    HindII         .         .
CAATTCTAGGAGAAGATTACACTAGTCAACCATGAGTGAAACATACGTGT
                                M  S  E  T  Y  V

         .         .         .         .         .
CTGAGAAAAGTCCAGGAGTGATGGCTAGCGGAGCGGAGCTGATTCCTGCC      500
S  E  K  S  P  G  V  M  A  S  G  A  E  I  I  R  A        23

         .         .         .         .         .
GCCGACATTCAAACGGCGCAGGCACGAATTTCCTCCGTCATTGCACCAAC
 A  D  I  Q  T  A  Q  A  R  I  S  S  V  I  A  P  T

         .         .         .         .         .
TCCATTGCAGTATTGCCCTCGTCTTTCTGAGGAAACCGGAGCGGAAATCT      600
  P  L  Q  Y  C  P  R  I  S  I  E  T  G  A  E  I         56

         .         .         .         .         .
ACCTTAAGCGTGAGGATCTGCAGGATGTTCGTTCCTACAAGATCCGCGGT
Y  L  K  R  E  D  L  Q  D  V  R  S  Y  K  I  R  G

         .         .         .         .         .
GCGCTGAACTCTGGAGCGCAGTCACCCCAAGAGCAGCGCGATGCAGGTAT      700
 A  L  N  S  G  A  Q  S  P  Q  E  Q  R  D  A  G  I       90

         .      BstEII       .         .         .
CGTTGCCGCATCTGCAGGTAACCATGCCCAGGGCGTGGCCTATGTGTGCA
  V  A  A  S  A  G  N  H  A  Q  G  V  A  Y  V  C

         .         .         .         .         .
AGTCCTTGGGCGTTCAGGGACGCATCTATGTTCCTGTGCAGACTCCAAAG      800
K  S  L  G  V  Q  G  R  I  Y  V  P  V  Q  T  P  K       123

         .         .         .         .         .
CAAAAGCGTGACCGCATCATGGTTCACGGCGGAGAGTTTGTCTCCTTGGT
 Q  K  R  D  R  I  M  V  H  G  G  E  F  V  S  L  V

         .         .         .         .         .
GGTCACTGGCAATAACTTCGACGAAGCATCGGCTGCAGCGCATGAAGATC      900
  V  T  G  N  N  F  D  E  A  S  A  A  A  H  E  D        156

         .         .         .         .         .
CAGAGCGCACCGGCGCAACGCTGATCGAGCCTTTCGATGCTCGCAACACC
A  E  R  T  G  A  T  L  I  E  P  F  D  A  R  N  T

         .         .        BglII      .         .
GTCATCGGTCAGGGCACCGTGGCTGCTGAGATCTTGTCGCAGCTGACTTC     1000
 V  I  G  Q  G  T  V  A  A  E  I  L  S  Q  L  T  S      190

         .         .         .         .         .
CATGGGCAAGAGTGCAGATCACGTGATGGTTCCAGTCGGCGGTGGCGGAC
  M  G  K  S  A  D  H  V  M  V  P  V  G  G  G  G

         .         .         .         .         .
```

TABLE 6-continued

Mutant 14 (SEQ ID NO:12)

```
TTCTTGCAGGTGTGGTCAGCTACATGGCTGATATGGCACCTCGCACTGCG   1100
L  L  A  G  V  V  S  Y  M  A  D  M  A  P  R  T  A     223

         .         .         .         .         .
ATCGTTGGTATCGAACCAGCGGGAGCAGCATCCATGCAGGCTGCATTGCA
 I  V  G  I  E  P  A  G  A  A  S  M  Q  A  A  L  H

         .         .         .         .         .
CAATGGTGGACCAATCACTTTGGAGACTGTTGATCCCTTTGTGGACGGCG   1200
 N  G  G  P  I  T  L  E  T  V  D  P  F  V  D  G       256

         .        BglII      .         .         .
CAGAGGTCAAACGTGTCGGAGATCTCAACTACACCATCGTGGAGAAGAAC
A  E  V  K  R  V  G  D  L  N  Y  T  I  V  E  K  N

         .         .         .         .         .
CAGGGTCGCGTGCGCATGATGAGCGCGACCGAGGGCGCTGTGTGTACTGA   1300
 Q  G  R  V  R  M  M  S  A  T  E  G  A  V  C  I  E     290

         .         .         .         .         .
GATGCTCGATCTTTACCAAAACGAAGGCATCATCGCGGAGCCTGCTGGCG
  M  L  D  L  Y  Q  N  E  G  I  I  A  E  P  A  G

         .         .         .         .         .
CGCTGTCTATCGCTGGGTTGAAGGAAATGTCCTTTGCACCTGGTTCTGTC   1400
A  L  S  I  A  G  L  K  E  M  S  F  A  P  G  S  V     323
                                          --------------

         .         .         .         .         .
GTGGTGTGCATCATCTCTGGTGGCAACAACGATGTGCTGCGTTATGCGGA
 V  V  C  I  I  S  G  G  N  N  D  V  L  R  Y  A  E
--------------------------------------------------

         .         .         .         .         .
AATCGCTGAGCGCTCCTTGGTGCACCGCGGTTCGAAGCACTACTTCTTGG   1500
  I  A  E  R  S  L  V  H  R  G  S  K  N  Y  F  L     356
--------------------------------------------------

         .         .         .         .   EcoRV.
TGAACTTCCCGCAAAAGCCTGGTCAGTTGCGTCACTTCCTGGAAGATATC
V  N  F  P  Q  K  P  G  Q  L  R  H  F  L  E  D  I
--------------------------------------------------

         .         .         .         .         .
CTGGGACCGGATGATGACATCACGCTGTTTGAGTACCTCAAGCGCAACAA   1600
 L  G  P  D  D  D  I  T  L  F  E  Y  L  K  R  N  N     390
--------------------------------------------------

         .         .         .         .         .
CCGTGAGACCGGTACTGCGTTGGTGGGTATTCACTTGAGTGAAGCATCAG
  R  E  T  G  T  A  L  V  G  I  H  L  S  E  A  S
--------------------------------------------------

         .         .         .         .         .
GATTGGATTCTTTGCTGGAACGTATGGAGGAATCGGCAATTGATTCCCGT   1700
G  L  D  S  L  L  E  R  M  E  E  S  A  I  D  S  R     423
--------------------------------------------------

         .         .         .         .         .
CGCCTCGAGCCGGGCACTCCTGAGTACGAATACTTGACCTAAACATAGCT
 R  L  E  P  G  T  P  E  Y  E  Y  L  T  *
---------------------------------------

         .         .         .         .         .
GAAGGCCACCTCAATCGAGGTGGCCTTTTTCTAGTTTCGGGTCAGGATCG   1800
                                                      436

         .         .         .         .         .
CAAAGCCCCACGGCTGAAGGGTTGTGGAGGTGTCGGTGACGGTGGGGGAA

         .         .         .         .         .
GTGAAGCTGTAAATCAGCTCGCCGCCAAGCGGGACGGTGATGGTGTCGTC   1900

         .    EcoRI    .
GGAGAAATTCGCCAGAATTCGGCCG
```

We claim:

1. A method for the microbial production of L-isoleucine, comprising (A) recombinantly preparing a microorganism having a mutated threonine dehydratase gene by replacing at least one base in the region of the gene that encodes an allosteric domain of the threonine dehydratase, wherein said replacing at least one base results in deregulation of threonine dehydratase from L-isoleucine feedback inhibition, thereby producing a recombinant microorganism, and (B) culturing the recombinant microorganism to produce L-isoleucine.

2. The method of claim 1, wherein the microorganism is *Corynebacterium glutamicum.*

3. The method of claim 1, wherein the recombinant microorganism is obtained by growing the microorganism on a solid medium which contains L-isoleucine and L-valine, and then selecting colonies with an altered morphology.

4. The method of claim 1, wherein said mutated threonine dehydratase gene is obtained from *Escherichia coli.*

5. The method of claim 1, wherein said mutated threonine dehydratase gene is obtained from *Corynebacterium glutamicum.*

6. The method of claim 1, wherein said replacing is selected from the group consisting of (i) replacing alanine in position 257 of SEQ ID NO: 8 with glycine and (ii) replacing methionine in position 199 of SEQ ID NO: 10 with valine.

7. The method of claim 1, wherein said replacing includes replacing, in SEQ ID NO:10, (a) histidine in position 278 with arginine and (b) leucine in position 351 with serine.

8. The method of claim 3, wherein acetohydroxy acid synthase activity of the microorganism has been inhibited by the L-valine contained in the solid medium.

9. The method of claim 3, wherein the medium comprises a substance for inducing the threonine dehydratase gene.

10. The method of claim 9, wherein said substance is isopropyl-β-D-thiogalactopyranoside.

11. An isolated DNA that encodes a threonine dehydratase that is insensitive to L-isoleucine feedback, said DNA prepared by replacing at least one base in the region of the DNA that encodes an allosteric domain of the threonine-dehydratase.

12. The DNA of claim 11, comprising a nucleotide sequence selected from the group consisting of SEQ ID NO:1, SEQ ID NO:3, and SEQ ID NO:5.

13. The DNA of claim 11, comprising a nucleotide sequence selected from the group consisting of SEQ ID NO:7, SEQ ID NO:9, and SEQ ID NO:11.

14. A cell comprising the DNA of claim 11.

15. A vector comprising DNA that encodes a threonine dehydratase that is insensitive to L-isoleucine feedback, said DNA prepared by replacing at least one base in the region of the DNA that encodes an allosteric domain of the threonine-dehydratase.

16. A vector according to claim 15, further comprising a promoter, inducible by isopropyl-β-D-thiogalactopyranoside, that is operably associated with said DNA.

17. A cell comprising a vector according to claim 15.

18. A cell comprising a vector according to claim 16.

19. The cell as claimed in claim 18, wherein said cell exhibits acetohydroxy acid synthase activity which can be inhibited by L-valine.

20. The cell as claimed in claim 18, which is an *Escherichia coli* cell.

21. The cell as claimed in claim 18, which is a *Corynebacterium glutamicum* cell.

22. The cell as claimed in claim 18, wherein said cell does not synthesize threonine dehydratase that is sensitive to L-isoleucine feedback.

* * * * *